United States Patent
Nakashima et al.

[11] Patent Number: 5,906,795
[45] Date of Patent: May 25, 1999

[54] PIPETTING APPARATUS

[75] Inventors: Hidetoshi Nakashima, Osaka; Mikio Hojo, Higashiosaka; Masashi Yasuda, Hirakata, all of Japan

[73] Assignee: Sanyo Electric Co., Ltd., Osaka, Japan

[21] Appl. No.: 08/833,526

[22] Filed: Apr. 7, 1997

[30] Foreign Application Priority Data

| Apr. 8, 1996 | [JP] | Japan | 8-085435 |
| Apr. 11, 1996 | [JP] | Japan | 8-089488 |
| Apr. 16, 1996 | [JP] | Japan | 8-094103 |
| Dec. 26, 1996 | [JP] | Japan | 8-348032 |
| Feb. 20, 1997 | [JP] | Japan | 9-036028 |
| Feb. 20, 1997 | [JP] | Japan | 9-036029 |
| Feb. 20, 1997 | [JP] | Japan | 9-036030 |
| Feb. 20, 1997 | [JP] | Japan | 9-036031 |

[51] Int. Cl.$^6$ ................................. B01L 3/02
[52] U.S. Cl. ............... 422/100; 422/101; 422/103; 422/104; 73/864.13; 73/864.32
[58] Field of Search ........................ 422/100, 101, 422/103, 104; 73/864.13, 864.32

[56] References Cited

U.S. PATENT DOCUMENTS

| 4,282,745 | 8/1981 | Burr | 73/61.4 |
| 4,427,483 | 1/1984 | Sachs et al. | 156/345 |
| 5,305,650 | 4/1994 | Koike et al. | 73/864.21 |
| 5,620,660 | 4/1997 | Belgardt et al. | 422/100 |
| 5,620,661 | 4/1997 | Schurbrock | 422/100 |
| 5,672,320 | 9/1997 | Ritter | 422/100 |

FOREIGN PATENT DOCUMENTS

| 0 226 867 | 7/1987 | European Pat. Off. . |
| 0 282 076 | 9/1988 | European Pat. Off. . |
| 0 763 739 | 3/1997 | European Pat. Off. . |
| 2 609 808 | 7/1988 | France . |
| 2 703 466 | 10/1994 | France . |

*Primary Examiner*—Harold Y. Pyon
*Attorney, Agent, or Firm*—Nikaido, Marmelstein, Murray & Oram LLP

[57] ABSTRACT

A chuck mechanism (2) for holding a pipette head (3) is attached to an output end of a reciprocating drive mechanism (1). A chuck control mechanism (5) for controlling the head holding and releasing operations of the chuck mechanism (2) is disposed at one side of each of head support members (41) of a head stowing device (4) for accommodating replaceable pipette heads (3). The chuck control mechanism (5) comprises a control piece (54) engageable with and disengageable from the chuck mechanism (2) for effecting the holding and releasing operations, and a plurality of magnets (81), (82), (8) for reciprocatingly driving the control piece (54) with the reciprocating movement of the chuck mechanism (2) when the pipette head (3) as held by the chuck mechanism (2) is thereby moved toward or away from the head support member (41). The pipetting apparatus is adapted to automatically and rapidly replace the pipette head by another.

14 Claims, 22 Drawing Sheets

PIPETTING APPARATUS

FIELD OF THE INVENTION

The present invention relates to pipetting apparatus for use in various kinds of analyses such as immunoassays and DNA analyses for automatically placing specified quantities of reagent into containers containing samples.

BACKGROUND OF THE INVENTION

For example in an immunoassay, a sample in a container is tested for an immunoreaction first by placing a liquid such as physiological saline into the container and then placing a reagent thereinto. FIG. 24 shows a pipetting apparatus conventionally used for placing such a liquid and reagent (hereinafter referred to collectively as the "reagent") into a container.

The illustrated pipetting apparatus comprises a pipette table 90 for mounting a reaction container 7 thereon, a head drive device 9 mounted on the table 90 and a pipette head 91 attached to the output end of the drive device 9. The pipette head 91 is connected to a plunger mechanism (not shown), and has a pipette tip 92 fitted to its lower end and directed downward for drawing in and discharging a reagent.

The reagent is placed into each of cavities 71 of the reaction container 7 by controlling the drive device 9 by a controller 93 to bring the pipette head 91 close to the container cavity 71 and drawing off the reagent from the pipette tip 92 into the cavity 71.

When the reagent is to be diluted or mixed with another reagent 72 already placed in the cavity 71, the reagent to be added dropwise from the pipette tip 92 is brought into contact with the liquid surface of the reagent 72 within the cavity 71 to free the surface tension, whereby the reagent is drawn off.

If the pipette tip 92 itself comes into contact with the reagent 72 in the cavity 71 at this time, the reagent adhering to the tip 92 becomes mixed with other reagent in the subsequent pipetting step. Accordingly, the reagent within the pipette tip 92 needs to be drawn off with the extremity of the tip 92 positioned slightly above the liquid surface of the reagent 72.

Pipette tips of different capacities are used for applying the reagent in different quantities of 0.5 $\mu$l to 200 $\mu$l by the pipetting apparatus. Prepared for the apparatus are a pipette head of small inside diameter for mounting pipette tips having a small capacity of 0.5 $\mu$l to 10 $\mu$l, and a pipette head of large inside diameter for use with pipette tips having a large capacity of 5 $\mu$l to 200 $\mu$l, and these pipette heads are alternatively used by replacement.

With the conventional pipetting apparatus, however, the pipette head is fixed to the apparatus main body by fastening means as by screwing. The apparatus therefore has the problem that the procedure for replacing the pipette head is not only cumbersome but also difficult because the head is as small as about 20 mm in outside diameter.

When the reagent is to be diluted or mixed with the reagent 72 in each cavity 71 of the reaction container 7 as stated above, the pipette head 91 is lowered to position the pipette tip 92 as close to the liquid surface of the reagent 72 as possible, whereas since the liquid level of the reagent 72 differs from cavity to cavity, the liquid level in each cavity must be measured to adjust the level of the pipette tip 92. At this time, an accuracy of about 0.1 mm is required of the measurement of the reagent liquid level.

Although it is advantageous to use a laser measuring instrument from the viewpoint of accuracy of distance measurements, the instrument is not usable for transparent reagents or reagents which are likely to undergo a photochemical reaction since the reagent is irradiated with a laser beam in this case.

Accordingly, it is practice to measure the distance to the liquid surface of the reagent 72 by an ultrasonic sensor attached to one side of the pipette head 91 and to feedback the measurement to the control of the head drive device 9. The sensor emits ultrasonic waves toward the object of measurement, receives the ultrasonic waves returning upon reflection at the object and measures the time taken for the emitted waves to return to the sensor to determine the distance to the object based on the time measurement.

While the level of the pipette head is controlled according to the distance thus measured by the ultrasonic sensor, the pipette tip 92 is likely to become damaged when an erroneous movement is involved in measuring the distance for one cause or another and if the pipetting operation is continued based on the result of measurement then obtained. For example, in the case where the measurement obtained is greater than the distance to the bottom face of the cavity 71 of the reaction container 7, the controller for the head drive device 9 sets as a target position for lowering the pipette head 91 a position where the extremity of the pipette tip 92 will be located further below the bottom face of the container cavity 71, with the result that when the head is lowered, the extremity of the tip 92 comes into striking contact with the bottom face of the cavity 71, bending the end portion and rendering the tip unable to draw off the reagent. The impact resulting from the striking contact of the pipette tip 92 with the reaction container 7 is also likely to cause damage to the pipette head 91.

SUMMARY OF THE INVENTION

An object of the present invention is to provide a pipetting apparatus having a pipette head which is replaceable by another pipette head automatically and rapidly.

The present invention provides a pipetting apparatus comprising a container mount for installing thereon one or a plurality of containers for a reagent to be withdrawn from or placed in, a head stowing device having accommodated therein one or a plurality of pipette heads for drawing in and discharging the reagent, a drive device for reciprocatingly moving an output end between the container mount and the head stowing device, a chuck mechanism attached to the output end of the drive device for holding and releasing the pipette head, and a chuck control mechanism disposed in the vicinity of a head stowage or each of head stowages of the head stowing device for causing the chuck mechanism to perform the holding operation and the releasing operation with the movement of the chuck mechanism when the chuck mechanism is moved toward or away from one head stowage of the head stowing device.

With the pipetting apparatus of the invention, the chuck mechanism is reciprocatingly driven by the drive device, and the pipette head held by the chuck mechanism is released therefrom with the movement of the chuck mechanism to the head stowage of the head stowing device, while the pipette head is held by the chuck mechanism with its movement to the head stowage of the head stowing device. This assures automatic rapid replacement of one pipette head by another pipette head.

More specifically, the chuck control mechanism comprises a control piece engageable with and disengageable from the chuck mechanism to effect the holding operation and the releasing operation, and magnet means for moving the control piece with the movement of the chuck mechanism when the chuck mechanism moves the pipette head held thereby toward or away from one head stowage of the head stowing device.

For the replacement of the pipette head by another, the pipette head held by the chuck mechanism is first moved to the head stowage of the head stowing device which stowage is empty by operating the drive device. While the pipette head is being accommodated into the head stowage, the magnet means operates with the movement of the chuck mechanism, bringing the control piece into engagement with the chuck mechanism to start a releasing operation. A further movement of the chuck mechanism completes the releasing operation to release the pipette head from the chuck mechanism. The chuck mechanism is thereafter moved away from the head stowage by operating the drive device. The magnetic means operates with this movement, releasing the control piece from the chuck mechanism.

Next, the drive device is operated to move the chuck mechanism to the head stowage accommodating the desired pipette head. While the chuck mechanism is being joined to this pipette head in the head stowage, the magnet means operates with the movement of the chuck mechanism, bringing the control piece into engagement with the chuck mechanism for the start of a holding operation. A further movement of the chuck mechanism completes the holding operation, whereby the pipette head is held by the chuck mechanism. The drive device is thereafter operated to move the chuck mechanism away from the head stowage along with the pipette head. This movement operates the magnet means, whereby the control piece is released from the chuck mechanism.

According to another pipetting apparatus of the invention, the chuck control mechanism comprises drive magnet means movable along a specified path with the movement of the chuck mechanism when the chuck mechanism moves the pipette head held thereby toward or away from one head stowage of the head stowing device, driven magnet means disposed as opposed to the drive magnet means and reciprocatingly movable along a specified path by a magnetic attracting force or magnetic repulsive force produced between the drive magnet means and the driven magnet means with the movement of the drive magnet means, and a control piece connected to the driven magnet means and engageable with and disengageable from the chuck mechanism with the reciprocating movement of the driven magnet means to effect the holding operation and the releasing operation.

For the replacement of the pipette head by another in the pipetting apparatus described, the pipette head held by the chuck mechanism is first moved to the head stowage of the head stowing device which stowage is empty by operating the drive device. While the pipette head is being accommodated into the head stowage, the drive magnet means moves with the movement of the chuck mechanism, whereby the driven magnet means is moved by being subjected to a magnetic attracting force or magnetic repulsive force. This movement of the driven magnet means brings the control piece into engagement with the chuck mechanism to start a releasing operation. A further movement of the chuck mechanism completes the releasing operation to release the pipette head from the chuck mechanism. The chuck mechanism is thereafter moved away from the head stowage by operating the drive device. The drive magnetic means moves with this movement, causing the driven magnet means to be moved by a magnetic attracting force or magnetic repulsive force. This movement of the driven magnet releases the control piece from the chuck mechanism.

Next, the drive device is operated to move the chuck mechanism to the head stowage accommodating the desired pipette head. While the chuck mechanism is being joined to this pipette head in the head stowage, the drive magnet means moves with the movement of the chuck mechanism, whereby the driven magnet means is moved. This movement of the driven magnet means brings the control piece into engagement with the chuck mechanism for the start of a holding operation. A further movement of the chuck mechanism completes the holding operation, whereby the pipette head is held by the chuck mechanism. The drive device is thereafter operated to move the chuck mechanism away from the head stowage along with the pipette head. This movement moves the drive magnet means, whereby the driven magnet means is moved by being subjected to a magnetic attracting force or magnetic repulsive force. This movement of the driven magnet means releases the control piece from the chuck mechanism.

More specifically, the chuck mechanism 2 comprises a shaft 21 attached to the output end of the drive device, a plurality of chuck jaws 23, 23 pivoted to an end portion of the shaft 21 for clamping the pipette head 3, a slide sleeve 22 fitting around the shaft 21 and slidable thereon for opening and closing the chuck jaws 23, 23, and holding means movable with the sliding movement of the slide sleeve 22 for holding the slide sleeve 22 at a first slid position wherein the chuck jaws 23, 23 are open and a second slid position wherein the chuck jaws 23, 23 are closed.

To replace the pipette head by another in the pipetting apparatus having the construction specifically stated, the pipette head held by the chuck mechanism is first moved to the head stowage of the head stowing device which stowage is empty by operating the drive device. While the pipette head is being accommodated into the head stowage, the chuck control mechanism operates, causing the chuck mechanism to perform a releasing operation. More specifically, the slide sleeve 22 constituting the chuck mechanism is slidingly moved in one direction by the operation of the chuck control mechanism, whereby the chuck jaws 23, 23 are opened. The movement of the slide sleeve 22 to the first slid position releases the pipette head from the chuck mechanism. With the movement of the slide sleeve 22, the holding means operates to hold the sleeve 22 at the first slid position.

The drive device thereafter operates to move the chuck mechanism away from the head stowage.

Next, the drive device operates to move the chuck mechanism to the head stowage accommodating the desired pipette head. While the chuck mechanism is being joined to this pipette head in the head stowage, the chuck control mechanism operates, causing the chuck mechanism to perform a holding operation. More specifically, the slide sleeve 22 constituting the chuck mechanism is slidingly moved in a direction opposite to the above-mentioned one direction by the operation of the chuck control mechanism. This movement closes the chuck jaws 23, 23. The slide sleeve 22 moves to the second slid position, whereby the pipette head is held by the chuck mechanism. With the movement of the slide sleeve 22, the holding means operates to hold the sleeve 22 in the second slid position.

The drive device thereafter operates to move the chuck mechanism away from the head stowage along with the pipette head, followed by a predetermined pipetting operation.

Thus, the slide sleeve 22 constituting the chuck mechanism is retained by the holding means in its slid positions wherein the chuck jaws 23, 23 are held open and closed, so that the sleeve 22 is unlikely to become displaced during the movement of the chuck mechanism, consequently realizing reliable holding and releasing operations.

More specifically, the chuck mechanism 2 comprises a plurality of jaws 23, 23 for holding a base end of the pipette head 3 from therearound, and rotation preventing means is provided at a junction of the chuck mechanism 2 and the pipette head 3 for preventing the rotation of the pipette head 3 as held by the chuck mechanism 2.

The rotation preventing means is provided with means for adjusting the angle of rotation, relative to the chuck mechanism 2, of the pipette head 3 as held by the chuck mechanism.

To replace the pipette head by another in the construction specifically stated, the pipette head held to the chuck mechanism is first moved to the head stowage of the head stowing device which stowage is empty by operating the drive device. While the pipette head is being accommodated into the head stowage, the chuck control mechanism operates, causing the chuck mechanism to perform a releasing operation, whereby the pipette head is released from the chuck mechanism. The drive device thereafter operates to move the chuck mechanism away from the head stowage.

Next, the drive device operates to move the chuck mechanism to the head stowage accommodating the desired pipette head. While the chuck mechanism is being joined to this pipette head in the head stowage, the chuck control mechanism operates, causing the chuck mechanism to perform a holding operation. Thus, the pipette head is held by the chuck mechanism.

At this time, the head 3 is clamped by the jaws 23, 23 of the chuck mechanism 2 from therearound and joined to the mechanism 2. In this state, the pipette head 3 is prevented from rotating relative to the chuck mechanism 2 by the rotation preventing means. The drive device thereafter operates, moving the chuck mechanism away from the head stowage along with the pipette head. A predetermined pipetting operation then follows.

The pipette head 3 as held by the chuck mechanism is prevented from rotating as described above and therefore remains in a specified position with respect to the angle of rotation without displacement. Accordingly, the pipette head 3 can be moved in the specified position to the reaction container 7 for pipetting. Especially in the case where the pipette head is equipped with a plurality of pipette tips as arranged in a row, an error in the position of the head with respect to the angle of rotation would lead to an error in the pipetting operation, whereas the apparatus of the invention is free of such errors.

Further when the rotation preventing means is provided with means for adjusting the angle of rotation, the position of the pipette head 3 as held by the chuck mechanism 2 is adjustable with respect to the angle of rotation, with the result that an angular displacement, if occurring, can be corrected.

Stated specifically, the chuck mechanism 2 comprises a plurality of chuck jaws 23, 23 for holding the pipette head 3 and opening-closing means for opening and closing the chuck jaws 23, 23 with the reciprocating movement of the chuck mechanism 2 by the operation of the drive device 1. The chuck mechanism 2 further has coupled thereto first sensor means for detecting the pipette head 3 as joined to the chuck mechanism 2 and second sensor means for detecting the chuck jaws 23, 23 as closed by the opening-closing means. The first sensor means and the second sensor means have connected thereto means for notifying the operator of the result of detection obtained by each sensor means.

To replace the pipette head by another in the pipetting apparatus described, the pipette head held by the chuck mechanism is first moved to the head stowage of the head stowing device which stowage is empty by operating the drive device. While the pipette head is being accommodated into the head stowage, the chuck control mechanism operates, causing the opening-closing means to open the chuck jaws 23, 23 which are closed, using the drive force of the drive device as motive power. This releases the pipette head from the chuck mechanism. The drive device thereafter operates to move the chuck mechanism away from the head stowage.

Next, the drive device operates to move the chuck mechanism to the head stowage accommodating the desired pipette head. While the chuck mechanism is being joined to this pipette head in the head stowage, the chuck control mechanism operates, causing the opening-closing means to close the chuck jaws 23, 23 which are open, using the drive force of the drive device as motive power. As a result, the pipette head is held by the chuck mechanism. The drive device thereafter operates to move the chuck mechanism away from the head stowage along with the pipette head, followed by a specified pipetting operation.

In the foregoing holding operation of the chuck mechanism 2, the pipette head 3 is joined to the chuck mechanism 2, whereupon this state is detected by the first sensor means. When the opening-closing means closes the chuck jaws 23, 23, this state is detected by the second sensor beans. Accordingly, when these states are detected by the respective sensor means, this indicates that a normal holding operation has been performed. The specified pipetting operation then follows.

If one of these two states is not detected or neither of them is detected in the event of a fault occurring in the holding operation, the result is interpreted as indicating that a normal holding operation has not been effected. An alarm is then given when required, and no pipetting operation follows to ensure safety.

Another object of the present invention is to provide a pipetting apparatus wherein the extremity of the pipette tip is unlikely to collide with the reaction container even in the event of an error occurring in a distance measuring operation.

The present invention provides a pipetting apparatus which comprises a reciprocating drive device, a pipette head attached to an output portion of the device for drawing in and discharging a liquid, and a distance sensor provided at one side of the pipette head and directed downward for measuring the distance to an object, the distance sensor having connected thereto a control unit for controlling the operation of the drive device.

The control unit comprises a data memory having stored therein a limit distance in accordance with the distance to bottom faces of a plurality of cavities formed in a reaction container for the liquid to be placed in, a first controller for executing a procedure for measuring the distance to the liquid surface in the specified cavity of the reaction container for the liquid to be placed in, and a second controller for comparing the liquid surface distance obtained by the operation of the first controller with the limit distance stored in the data memory and executing a pipetting operation based on the limit distance when the liquid surface distance is greater than the limit distance.

With the pipetting apparatus of the invention, stored in the data memory as the limit distance is the distance to the bottom faces of the cavities formed in the reaction container, or a distance slightly smaller than this distance.

Before pipetting, the distance to the liquid surface in the specified cavity of the reaction container for a liquid to be placed in is measured first. If the container cavity contains no other liquid and is empty, the distance to the bottom face of the cavity is measured in this step. For the pipetting operation to be performed, the measured liquid surface distance is compared with the limit distance stored in the data memory. When involving no error, the liquid surface distance is unlikely to exceed the limit distance. As a result, a normal pipetting operation is executed based on the liquid surface distance measured.

On the other hand, if the liquid surface distance contains an error and is greater than the limit distance, the pipetting operation is performed using the limit distance as the liquid surface distance. It is therefore possible to avoid the situation wherein the extremity of the pipette tip descends further below the bottom face of cavity of the reaction container although the extremity may dip into the liquid in the container cavity, whereby the collision of the pipette tip is avoided. Consequently, the pipetting operation is to be performed at least to the minimum extent required.

When the limit distance stored in the data memory is a distance smaller than the distance to the bottom faces of the cavities formed in the reaction container, it is possible to minimize the likelihood of the pipette tip extremity dipping into the liquid in the container.

More specifically, the data memory has further stored therein a second limit distance in accordance with the distance to the upper surface of the reaction container for the liquid to be placed in, and the second controller compares the liquid surface distance obtained by the operation of the first controller with the second limit distance stored in the data memory and executes the pipetting operation based on the second limit distance as the liquid surface distance when the liquid surface distance is smaller than the second limit distance.

When the liquid surface distance contains an error and is smaller than the second limit distance, the second limit distance serves as the liquid surface distance for executing the pipetting operation. Accordingly, the pipetting operation can be performed with the pipette tip extremity positioned close to the reaction container to the greatest possible extent, whereby a normal pipetting operation is realized despite the possible error involved in measuring the distance.

Even in the event of an error occurring in the distance measuring operation, the apparatus of the invention performs a pipetting operation free of the likelihood that the pipette tip extremity will collide with the reaction container.

DETAILED DESCRIPTION OF EMBODIMENTS

Embodiments of the invention will be described below with reference to the drawings.

Overall Construction

Figure 1:
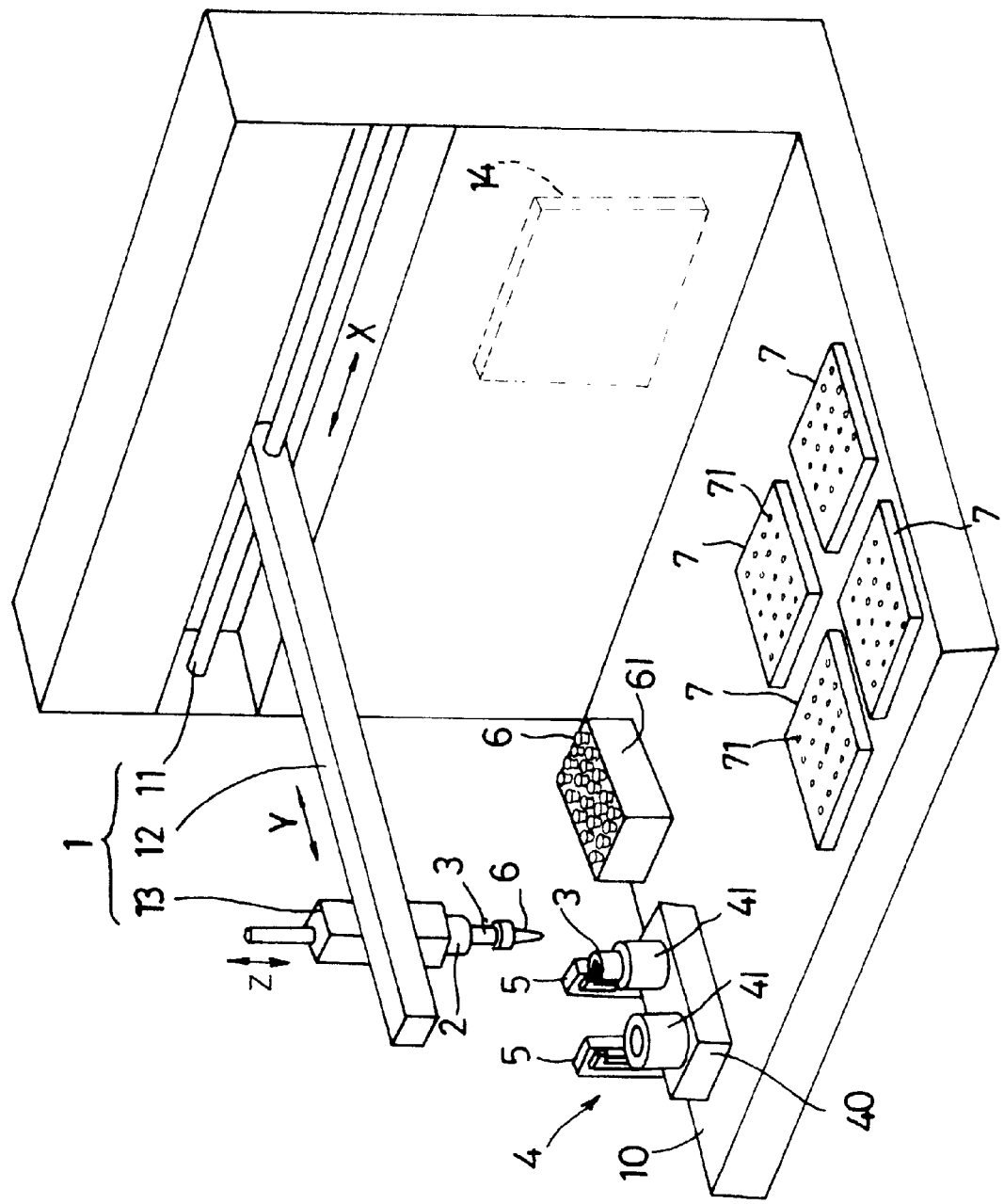
FIG. 1 is a perspective view showing the appearance of a pipetting apparatus embodying the invention.

With reference to FIG. 1 showing a pipetting apparatus embodying the invention, the apparatus comprises a reciprocating drive device 1 mounted on a pipette table 10 and comprising an X-axis drive mechanism 11, Y-axis drive mechanism 12 and Z-axis drive mechanism 13, and a chuck mechanism 2 attached to the output end of the Z-axis drive mechanism 13. As previously stated, a pipette head 3 is held by the chuck mechanism 2 and thereby connected to a plunger mechanism (not shown) for drawing in or discharging a reagent. The pipette head 3 has a lower end, to which a disposable pipette tip 6 is removably fitted. The drive device 1 and the plunger mechanism are operated under the control of a control circuit 14.

Positioned as specified on the pipette table 10 are a tip holder 61 having accommodated therein a plurality of disposable pipette tips 6, a head stowing device 4 holding a plurality of pipette heads 3, and a plurality of reaction containers 7. Each of the reaction containers 7 has a plurality of cavities 71 formed in its upper surface.

The head stowing device 4 comprises a plurality of head support members 41 corresponding in number to the number of pipette heads 3 to be stowed. Disposed at one side of each head support member 41 is a chuck control mechanism 5 for controlling the holding and releasing operations of the chuck mechanism 2.

Construction of Chuck Mechanism 2

Figure 2:
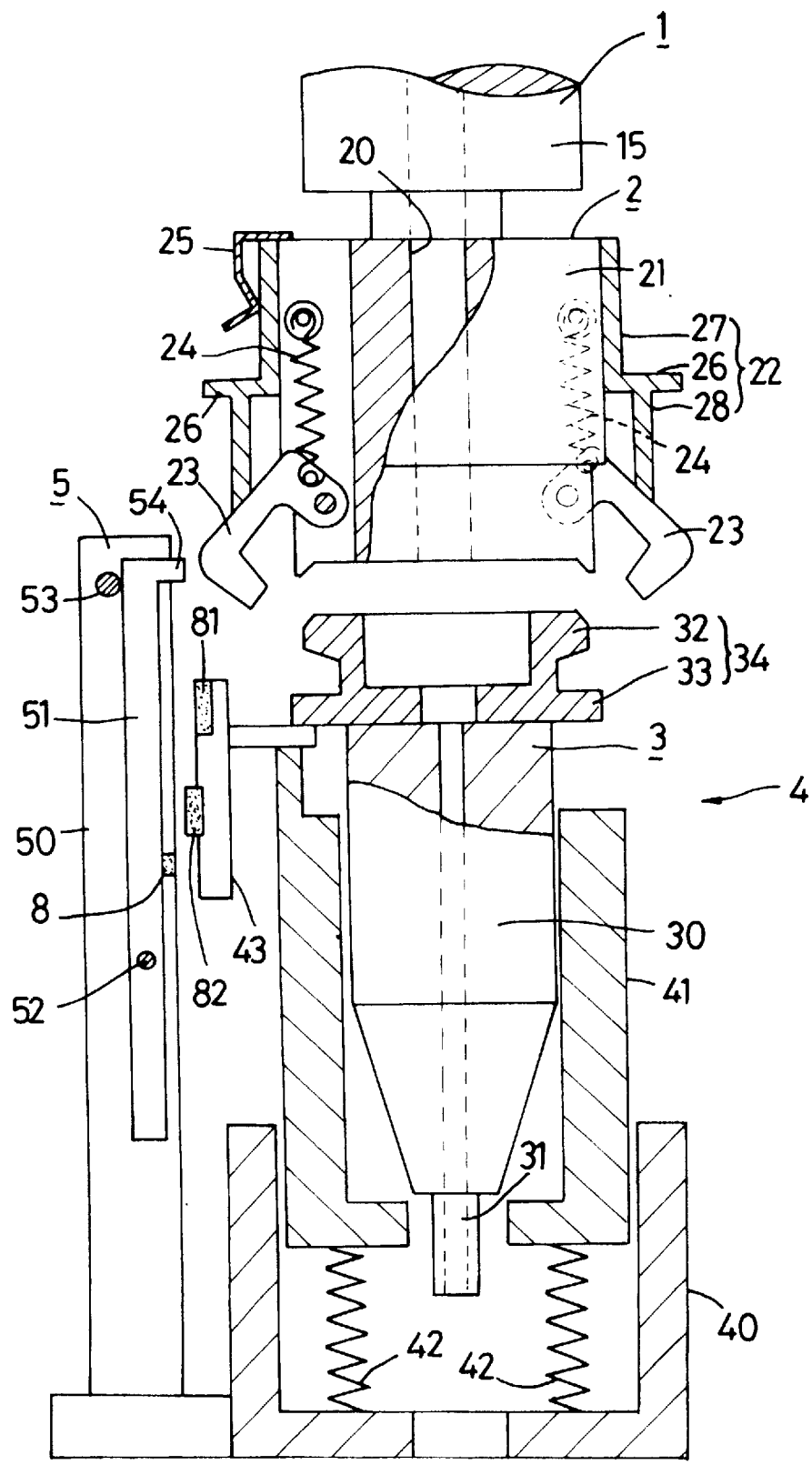
FIG. 2 is a front view partly broken away and showing main components of the apparatus on an enlarged scale.

Referring to FIG. 2, fixed to the output end 15 of the drive device 1 is a shaft 21 formed with a central bore 20 and having a slide sleeve 22 attached to the outer periphery of the shaft 21. The slide sleeve 22 comprises an upper half portion 27 slidably fitting around the shaft 21, a lower half portion 28 having a larger diameter than the upper half portion 27 and a flange 26 formed between these upper and lower portions 27, 28 and projecting outward. Attached to an upper portion of the shaft 21 is a holding spring 25 for pressing the slide sleeve 22 against the shaft 21. A pair of chuck jaws 23, 23 movable away from and toward each other (openable and closable) are pivoted to lower portions of the shaft 21 for holding the top portion of the pipette head 3. Each jaw 23 is biased toward the opening direction by a tension spring 24.

With the slide sleeve 22 held in a raised position as shown, therefore, the pair of chuck jaws 23, 23 are held open by being biased by the springs 24 in pressing contact with the lower end of the sleeve 22. When the slide sleeve 22 in this state is lowered, the jaws 23, 23 are depressed by the lower end of the sleeve 22 and closed against the tension springs 24.

Figure 7:
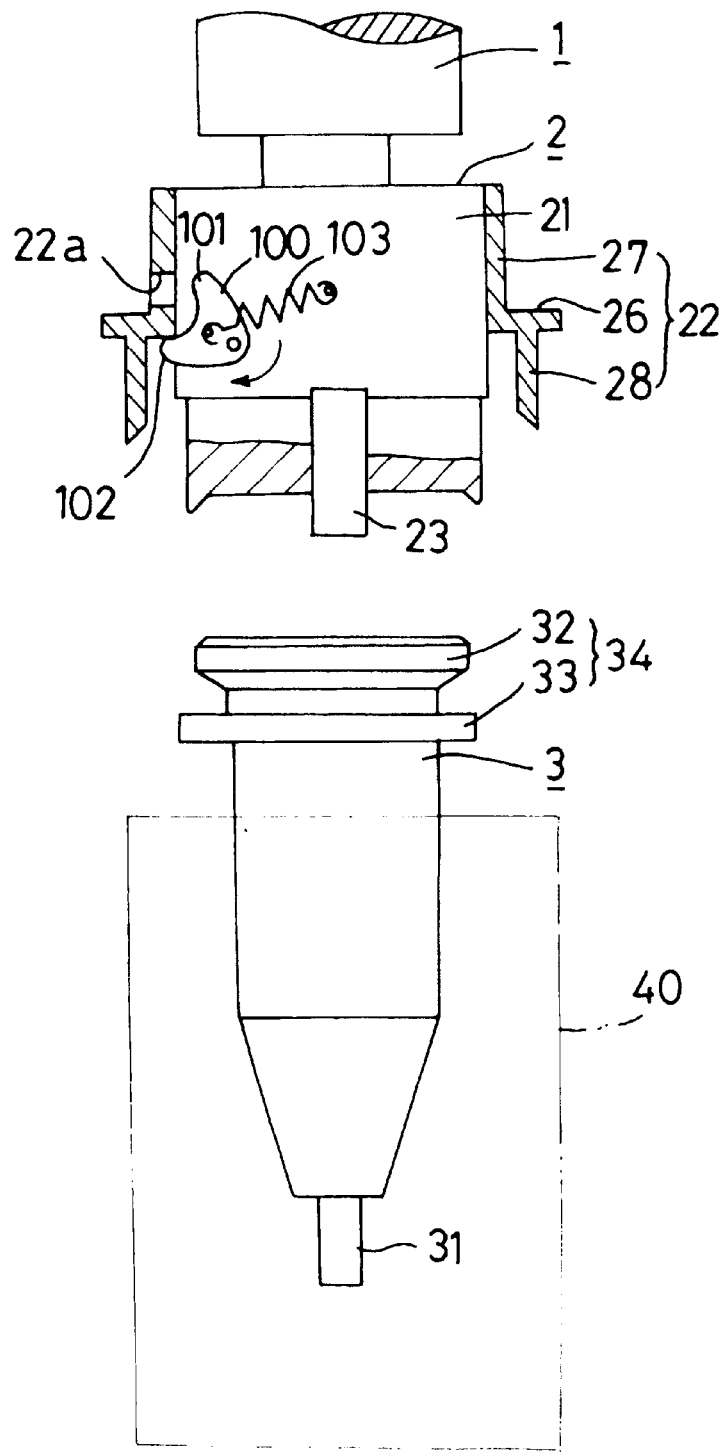
FIG. 7 is a front view partly broken away and showing a slide sleeve as held in a raised position.
Figure 8:
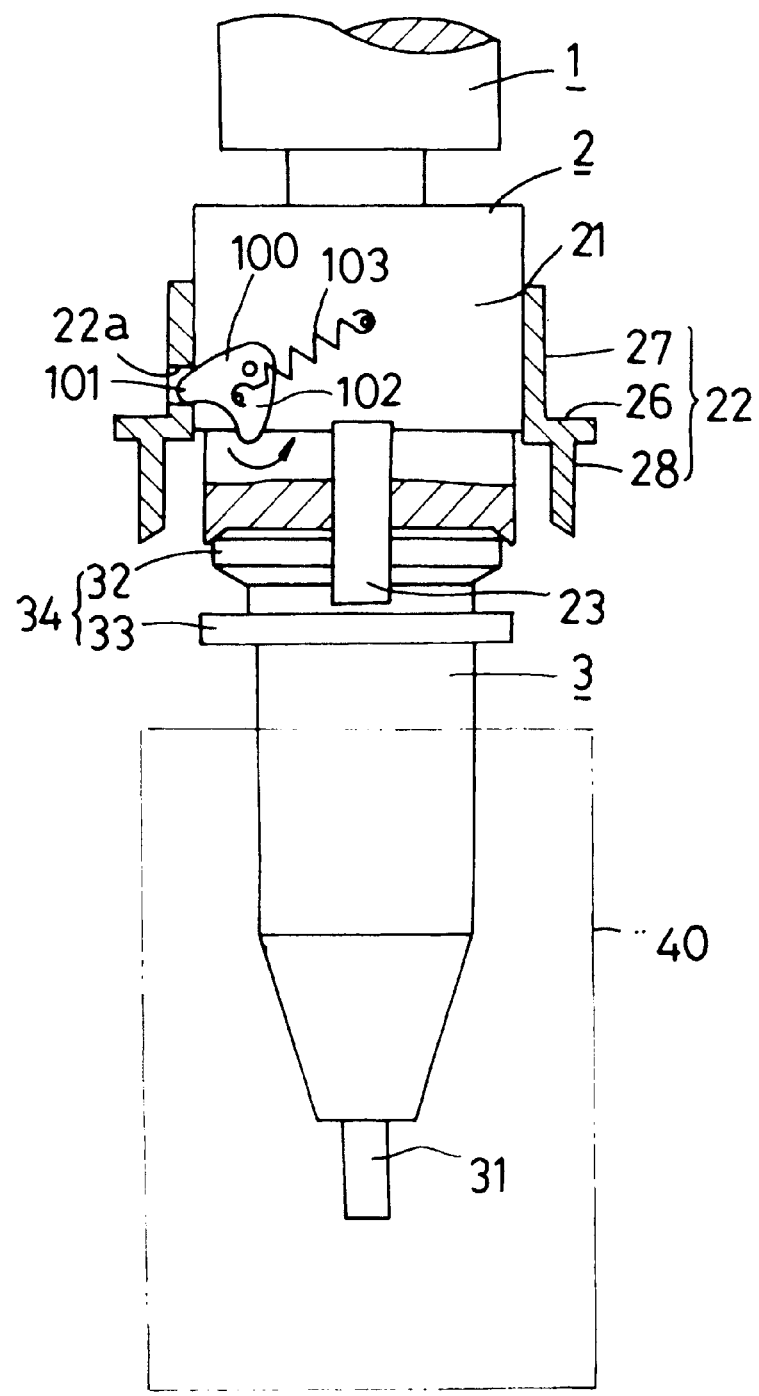
FIG. 8 is a front view partly broken away and showing the slide sleeve as held in a lowered position.

With the chuck mechanism 2 shown in FIG. 2, the spring 25 holds the slide sleeve 22 in its raised position and prevents the upward movement of the sleeve 22 in its lowered position. FIGS. 7 and 8 show an arrangement which ensures this function more reliably. An engaging piece 100 having first and second engaging portions 101, 102 is pivoted to the shaft 21 of the chuck mechanism 2. A tension spring 103 extending toward opposite sides of the pivot is provided between the engaging piece 100 and the shaft 21, whereby the piece 100 is biased into rotation in opposite directions with respect to a neutral position of pivotal movement. The slide sleeve 22 is formed at the lower end of its upper half portion 27 with a window 22a for permitting the first engaging portion 101 to engage in.

When the slide sleeve 22 is in its raised position shown in FIG. 7, the tension spring 103 biases the engaging piece 100 into clockwise rotation, with the second engaging portion 102 in bearing contact with the lower end of the upper half portion 27 of the sleeve 22, supporting the sleeve 22 from below by the action of the spring. As the slide sleeve 22 is moved to its lowered position from this state, the engaging piece 100 is depressed by the flange 26 of the sleeve 22, rotating counterclockwise against the spring 103 during the first half of the movement and under the action of the spring 103 during the second half of the movement. Upon the slide sleeve 22 reaching its lowered position, causing the chuck jaws 23, 23 to hold the pipette head 3 as seen in FIG. 8, the first engaging portion 101 of the engaging piece 100 engages in the window 22a of the sleeve 22. In this state, the tension spring 103 biasing the engaging piece 100 counterclockwise holds the slide sleeve 22 in its lowered position.

Construction of Pipette Head 3

With reference to FIG. 2, a connector 34 having a holdable portion 32 and a flange 33 is fixed to the top of main body 30 of the pipette head 3. The holdable portion 32 is to be held by the pair of chuck jaws 23, 23. The head main body 30 has a nozzle 31 projecting downward from its lower end. The pipette tip 6 is removably fittable to the nozzle 31.

When the pipette head 3 is held by the chuck mechanism 2, the shaft 21 of the mechanism 2 and the connector 34 of the head 3 engage with each other in intimate contact and in accurate alignment.

Construction of Rotation Preventing Mechanism

Figure 9:
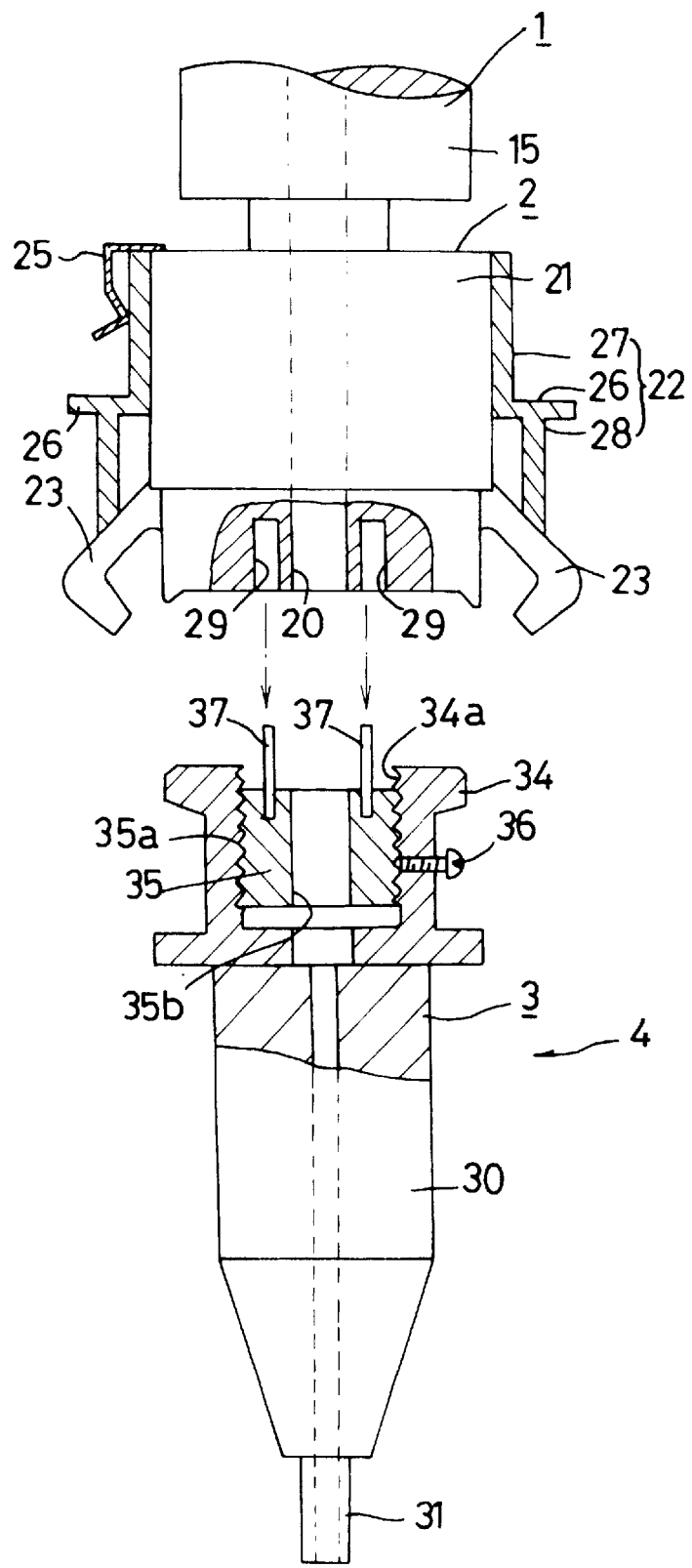
FIG. 9 is a front view partly broken away and showing the construction of rotation preventing means in a head released state.
Figure 10:
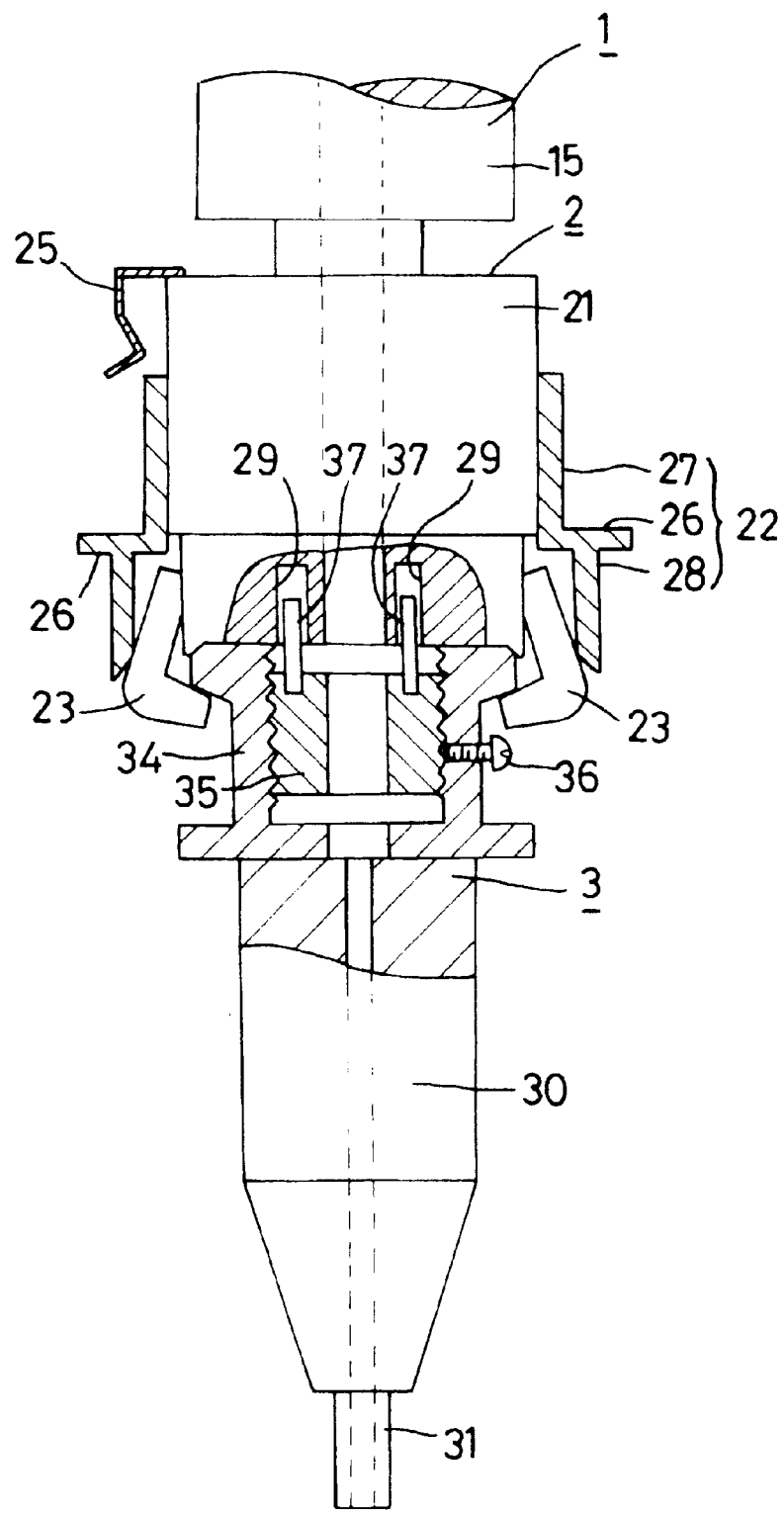
FIG. 10 is a front view partly broken away and showing the same in a head held state.

With the pipette head 3 held by the chuck mechanism 2 in the arrangement shown in FIG. 2, the head 3 is prevented from freely rotating about a vertical axis and retained in a fixed position with respect to the angle of rotation by the friction involved in the contact of the head 3 with the shaft 21 and the chuck jaws 23, 23 of the chuck mechanism 2, while FIGS. 9 and 10 show a mechanism for preventing the rotation of the pipette head 3 more effectively.

A screw member 35 is screwed in the central portion of the connector 34 of the pipette head 3. More specifically, the connector 34 is internally threaded as at 34a, the screw member 35 is externally threaded as at 35a, and the screw member 35 is screwed in the connector 34. The screw member 35 has a pair of retaining pins 37, 37 projecting vertically from its top and opposed to each other with its axis positioned therebetween. A lock screw 36 is screwed through a side portion of the connector 34 and has an inner end pressed into contact with the outer periphery of the screw member 35 to lock this member 35. The shaft 21 of the chuck mechanism 2 is vertically formed with a pair of pin bores 29, 29 positioned as opposed to the respective retaining pins 37, 37 and permitting the pins to fit in.

With the pipette head 3 held by the chuck mechanism 2 as seen in FIG. 10, the retaining pins 37, 37 on the head 3 fit in the respective pin bores 29, 29 in the chuck mechanism 2, retaining the head 3 against rotation.

Accordingly, even if the pipette head 3 or the chuck mechanism 2 is subjected to vibration or impact during the operation of the drive device 1 moving the head 3, the head 3 is unlikely to rotate, remaining in an accurate position with respect to the angle of rotation. Especially in the case where the pipette head 3 is so constructed as to be equipped with a plurality of pipette tips in a row, an error in the position of the head 3 with respect to the angle of rotation will result in an error in pipetting movement, whereas such errors are reliably avoidable by the provision of the rotation preventing mechanism described.

If the pipette head 3 is improperly positioned with respect to the angle of rotation for one cause or another, the angular displacement of the head 3 is corrected by loosening the lock screw 36 with the pipette head 3 held chucked and rotating the connector 34 relative to the screw member 35. At this time, the angular displacement of the head 3 is correctable, for example, with reference to the position of the cavities 71 of the reaction container 7 after moving the head 3 to the position of the container 7. The lock screw 36 is thereafter screwed in to lock the connector 34 to the screw member 35 against rotation relative thereto.

Construction of Safety Check Device

Figure 11:
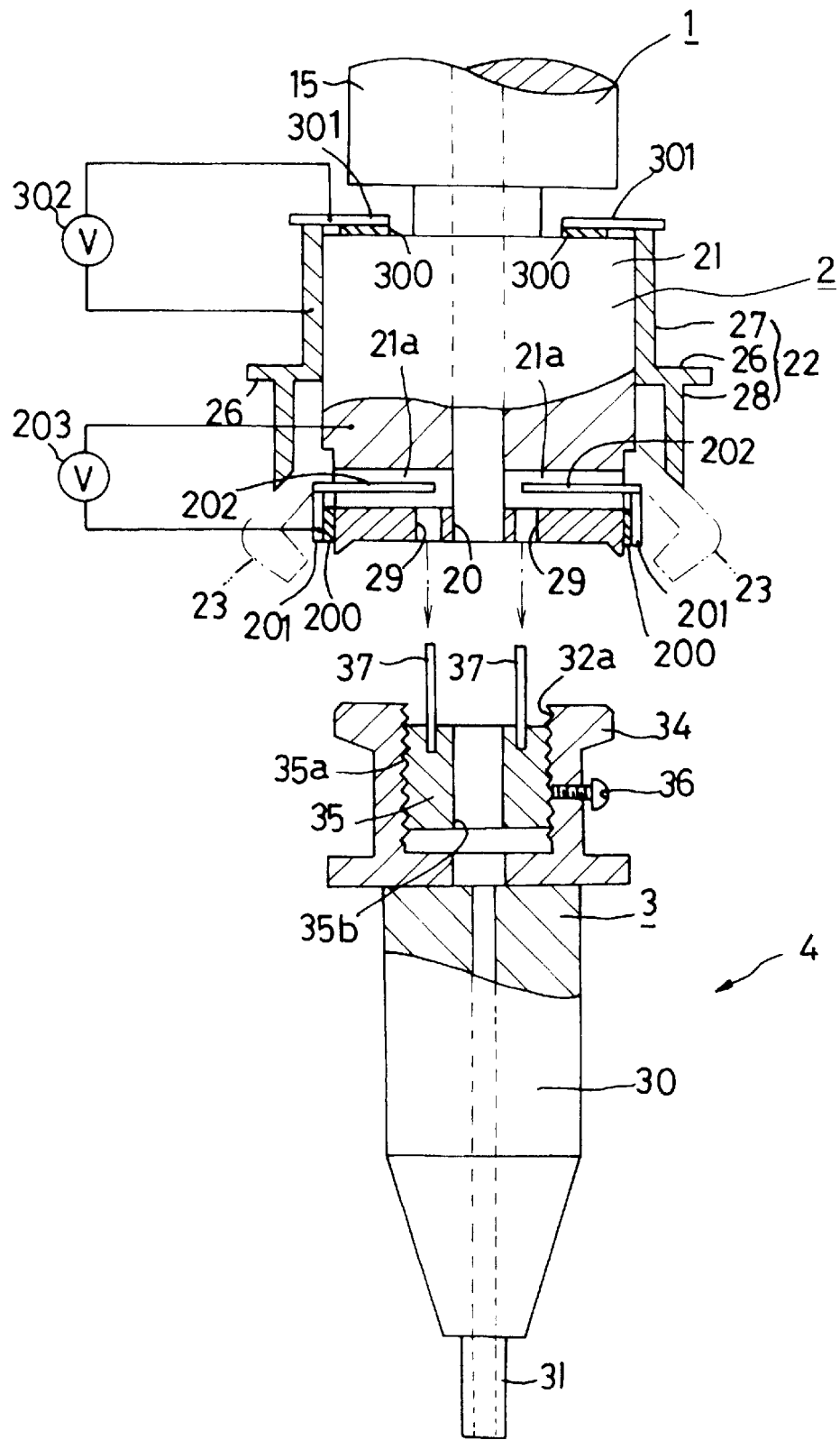
FIG. 11 is a front view partly broken away and showing the construction of a safety check device in the head released state.
Figure 12:
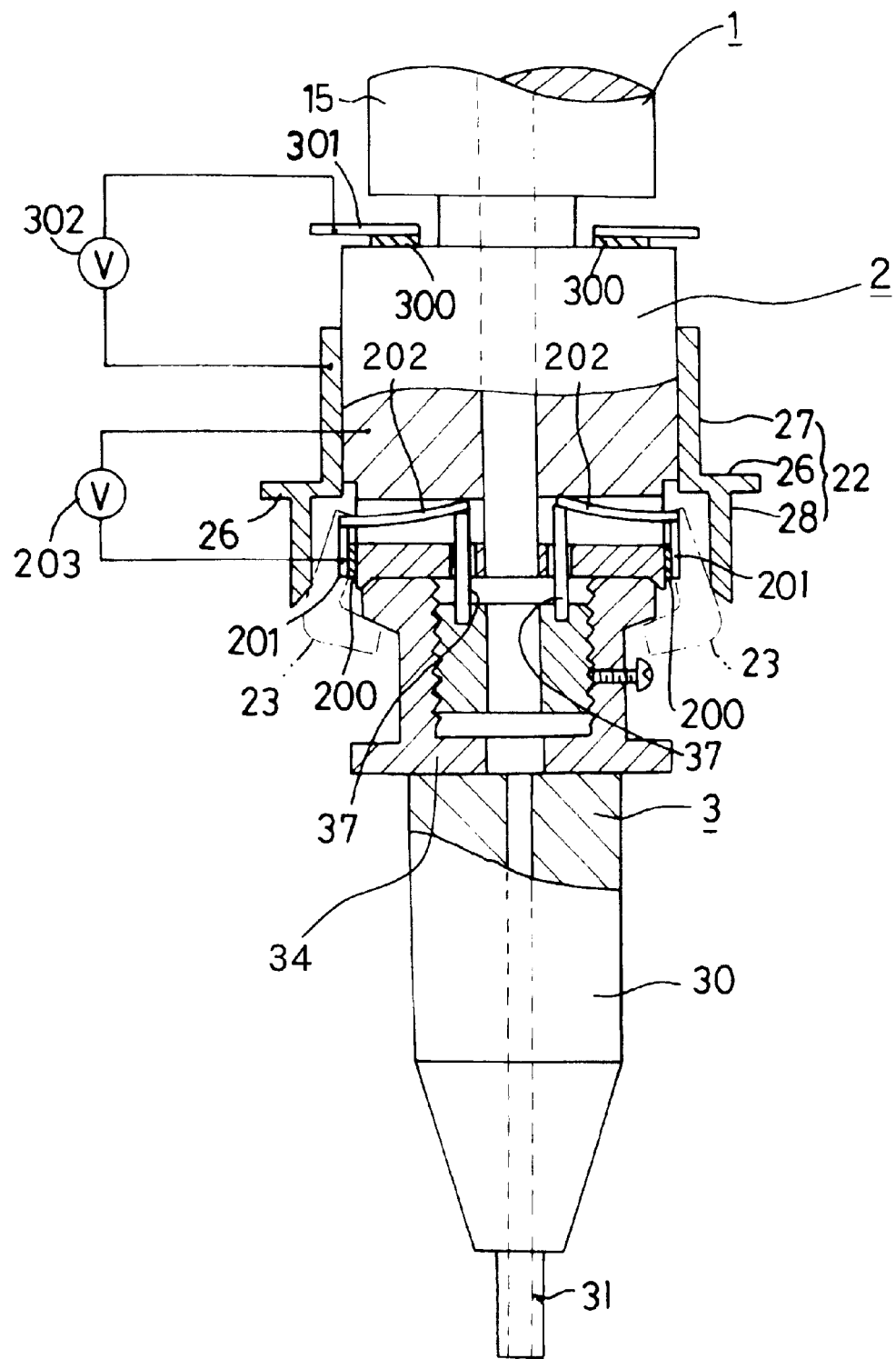
FIG. 12 is a front view partly broken away and showing the same in the head held state.

With reference to FIGS. 11 and 12, the chuck mechanism 2 is equipped with a safety check device for detecting the state in which the connector 34 of the pipette head 3 is joined to the shaft 21 of the chuck mechanism 2, and the state in which the chuck jaws 23, 23 are closed by the slide sleeve 22 of the chuck mechanism 2.

More specifically, the shaft 21 of the chuck mechanism 2 is formed with a pair of lateral bores 21a, 21a extending horizontally and positioned inwardly of (immediately above) the pair of pin bores 29, 29. To each of right and left opposite side portions of the shaft 21, a metal support piece 201 is secured with an insulator 200 interposed therebetween. A metal plate spring 202 horizontally extending into the lateral bore 21a to a position above the pin bore 29 is supported on the upper end of the support piece 201 in a cantilever manner. A first sensor 203 is connected to the support piece 201 and the shaft 21 for detecting electrical conduction therebetween. The first sensor connected to the support piece 201 on the right side and the shaft 21 is not shown in FIGS. 11 and 12.

A metal plate 301 has a base end secured to the top face of the shaft 21 at each of right and left end portions thereof, with an insulator 300 provided between the plate and the top face. The plate 301 has an outer end extending to a position above the slide sleeve 22. A second sensor 302 is connected to the metal plate 301 and the slide sleeve 22 for detecting electrical conduction therebetween. The second sensor connected to the metal plate 301 at right and the sleeve 22 is not shown in FIGS. 11 and 12.

As shown in FIG. 11, the slide sleeve 22 of the chuck mechanism 2 and the metal plate 301 are held in conduction by the contact of the upper end of the sleeve 22 with the metal plate 301 when the sleeve 22 is in its raised position with the pipette head 3 released from the chuck jaws 23, 23 as opened. The conductive state is detected by the second sensor 302.

On the other hand, the metal support piece 201 and the plate spring 202 are electrically insulated from the shaft 21, and the support piece 201 is held out of conduction with the shaft 21. This state is detected by the first sensor 203.

With reference to FIG. 12, the shaft 21 of the chuck mechanism 2 is thereafter joined to the connector 34 of the pipette head 3, with the slide sleeve 22 of the chuck mechanism 2 moved to its lowered position to cause the chuck jaws 23, 23 to hold the head 3. The sleeve 22 moved down is away from the metal plate 301 in this state and thereby held out of conduction with the plate 301. This state is detected by the second sensor 302.

On the other hand, the insertion of each of the retaining pins 37, 37 into the pin bore 29, 29 causes the pin upper end to push up the inner end of the plate. spring 202 into contact with the slide sleeve 22, whereby the metal support piece 201 and the shaft 21 are brought into conduction. This state is detected by the first sensor 203.

Thus, in the case where the first sensor 203 detects nonconduction with the second sensor 302 detecting conduction in the state of FIG. 11 wherein the pipette head 3 is released from the chuck mechanism 2, this state can be regarded as a normal released state. If the result of detection is otherwise, this indicates occurrence of a fault.

In contrast, when the first sensor 203 detects conduction with the second sensor 302 detecting nonconduction in the state of FIG. 12 wherein the pipette head 3 is held by the chuck mechanism 2, this state can be regarded as a normal held state. If the result of detection is otherwise, this indicates occurrence of a fault.

For example by an alarm lamp, the operator is informed of the fault detected, and the operation of the drive device 1 is automatically interrupted to ensure safety.

Construction of Head Stowing Device 4

With reference to FIG. 2, a head support member 41 adapted to accommodate or support the pipette head 3 is engaged in a head mount 40 upwardly and downwardly movably, as vertically elastically supported by springs 42.

Secured to an upper end portion of the head support member 41 is a magnet holder 43, which has a first drive magnet 81 and a second drive magnet 82 attached respectively to an upper portion and a lower portion thereof.

With the pipette head 3 accommodated in the head support member 41 of the head stowing device 4, the flange 33 of connector 34 of the head 3 bears on an end portion of the magnet holder 43 as illustrated, whereby the head 3 is supported.

Construction of Chuck Control Mechanism 5

A pivotal lever 51 is supported by a pivot 52 on an upright post 50 and extends alongside the post. Projecting from the upper end of the pivotal lever 51 is a control piece 54 engageable with the slide sleeve 22 of the chuck mechanism 2. A driven magnet 8 is mounted on the lever 51 at a position above the pivot 52.

The post 50 is provided with a stopper 53 for restraining the pivotal lever 51 from moving counterclockwise. The lever 51 is held in a vertical position with its upper end bearing on the stopper 53 as illustrated.

Figure 3:
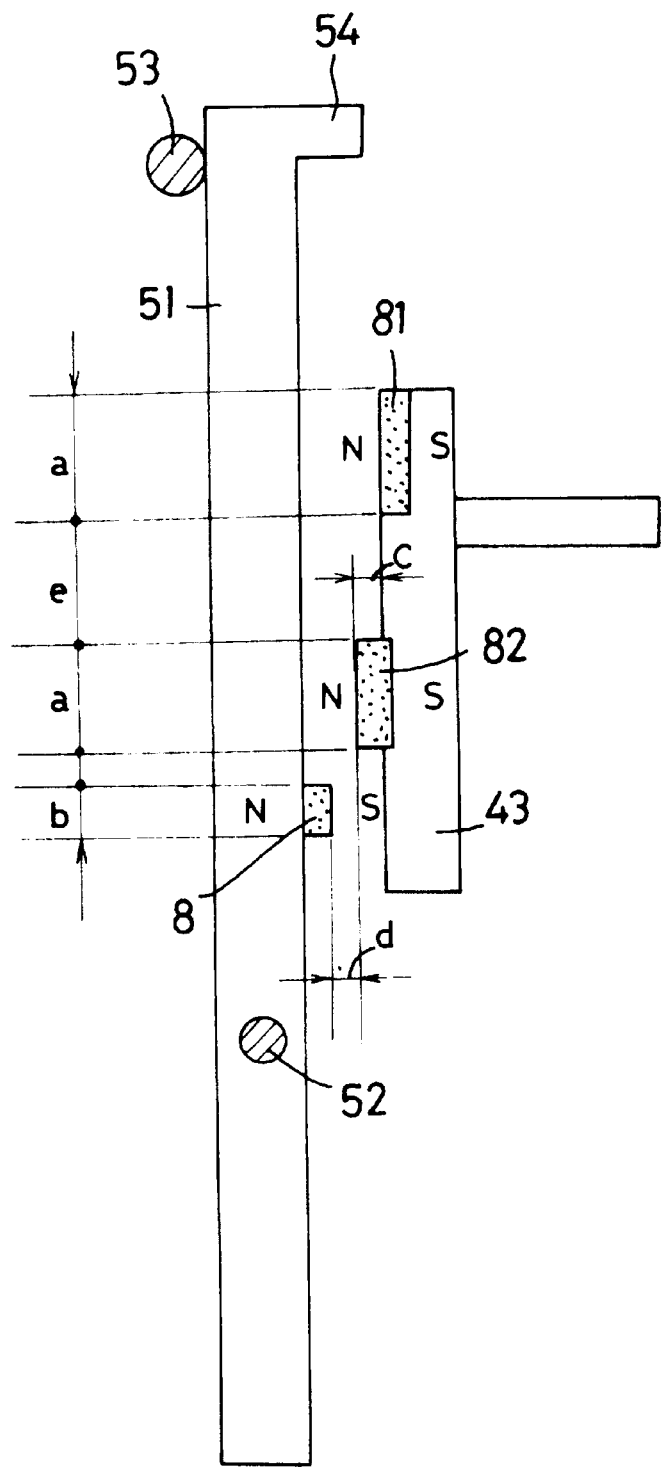
FIG. 3 is a diagram showing the polarity and position relationships between a first drive magnet, second drive magnet and driven magnet.

The first and second drive magnets 81, 82 on the holder 43 and the driven magnet 8 on the pivotal lever 51 are so oriented as to have the polar relation shown in FIG. 3. Stated more specifically, the first and second drive magnets 81, 82 are mounted on the holder 43 with their N poles facing toward the lever 51, while the S pole of the driven magnet 8 faces toward the holder 43.

These magnets 8, 81, 82 are so shaped and positioned relative to one another that the distances a, b, c, d and e shown in FIG. 3 are 3 mm, 2 mm, 1.2 mm, 1.7 mm and 5.6 mm, respectively. The magnets 8, 81, 82 have a surface magnetic flux density of 1200 gauss.

The above arrangement of the magnets 81, 82, 8 produces the following result. When the second drive magnet 82 and the driven magnet 8 are positioned in close proximity with each other at different levels as seen in FIG. 3, a repulsive state wherein the same poles of the two magnets repel each other predominates over an attracting state wherein the different poles of the magnets attract each other, consequently producing a repulsive force between the two magnets. On the other hand, when the second drive magnet 82 and the drive magnet 8 are opposed to each other face-to-face at the same level, the opposed different poles of the two magnets attract each other strongly to produce an attracting force between the two magnets. These phenomena occur similarly in the relationship between the first drive magnet 81 and the driven magnet 8.

Pipette Head Holding Operation

Figure 4:
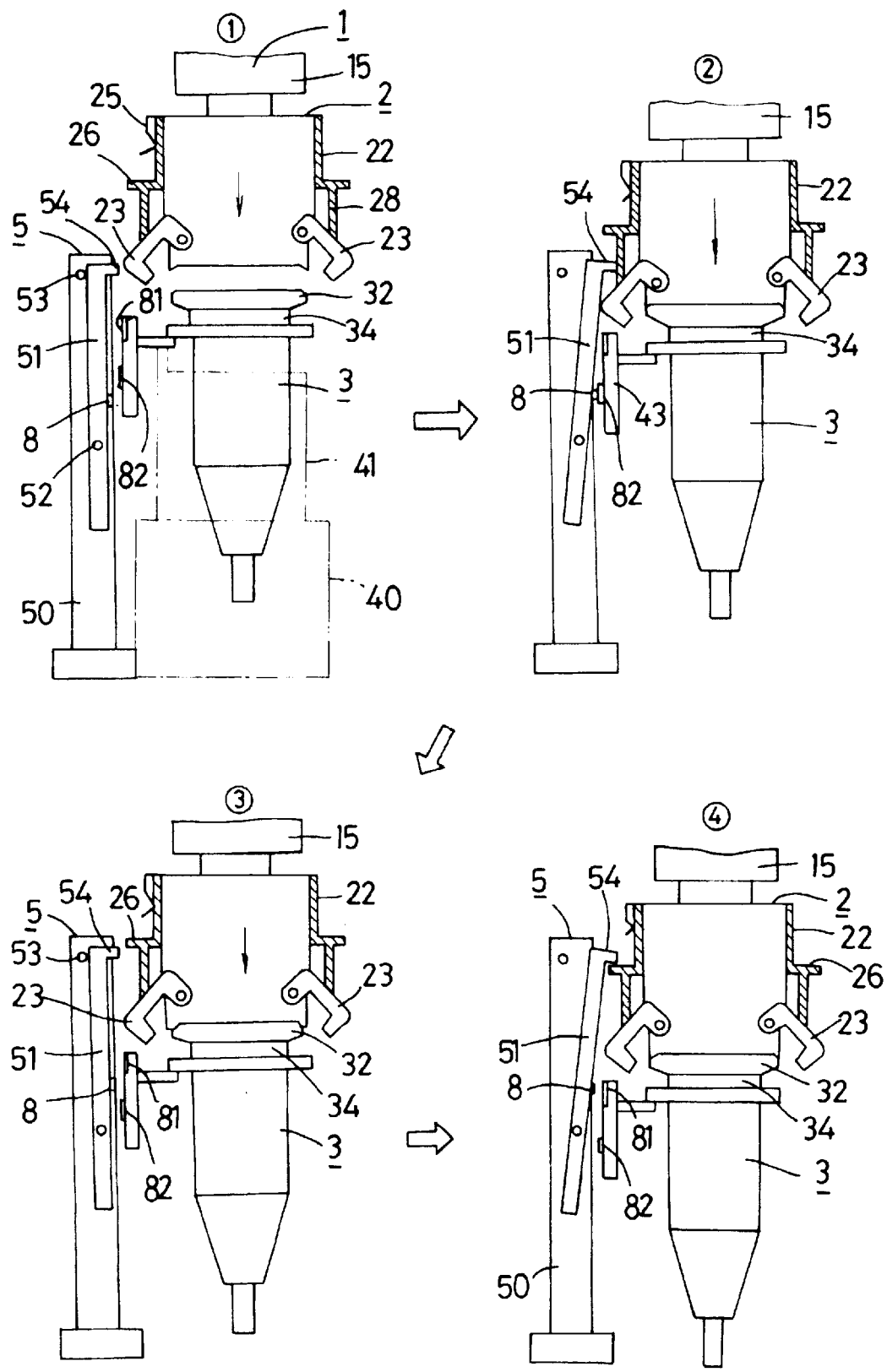
FIG. 4 is a diagram showing the first half of a head holding operation.

As shown in FIG. 4, step (1), the chuck mechanism carrying no pipette head is lowered toward the desired pipette head 3 stowed in the head support member 41, by operating the drive device 1. At this time, the slide sleeve 22 of the chuck mechanism 2 is held slidingly moved to its raised position by the holding spring 25, thereby causing the chuck jaws 23, 23 to be held open by the action of the tension springs 24. The head support member 41 is supported at a raised position by being biased by the springs 42, consequently positioning the second drive magnet 82 at a slightly higher level than the driven magnet 8. As a result, a repulsive force is produced between the driven magnet 8 and the second drive magnet 82 as previously stated, biasing the pivotal lever 51 counterclockwise into bearing contact with the stopper 53.

With reference to FIG. 4, step (2), the chuck mechanism 2 is further lowered, whereby the second drive magnet 82 is opposed to the driven magnet 8 to produce an attracting force between the two magnets.

This force slightly moves the pivotal lever 51 clockwise. When the chuck mechanism 2 is further lowered as seen in FIG. 4, step (3), an intermediate portion between the first drive magnet 81 and the second drive magnet 82 is opposed to the driven magnet 8, whereby a repulsive force occurs between the driven magnet 8 and the two drive magnets 81, 82. The repulsive force returns the pivotal lever 51 to its counterclockwise moved position.

The chuck mechanism 2 is further lowered, opposing the first drive magent 81 to the driven magnet 8 as seen in FIG. 4, step (4) to produce an attracting force between these magnets. This force turns the lever 51 clockwise again.

The movement of the pivotal lever 51 and descent of the chuck mechanism 2 described occur concurrently, permitting the control piece 54 of the lever 51 to move over the flange 26 of the slide sleeve 22.

Figure 5:
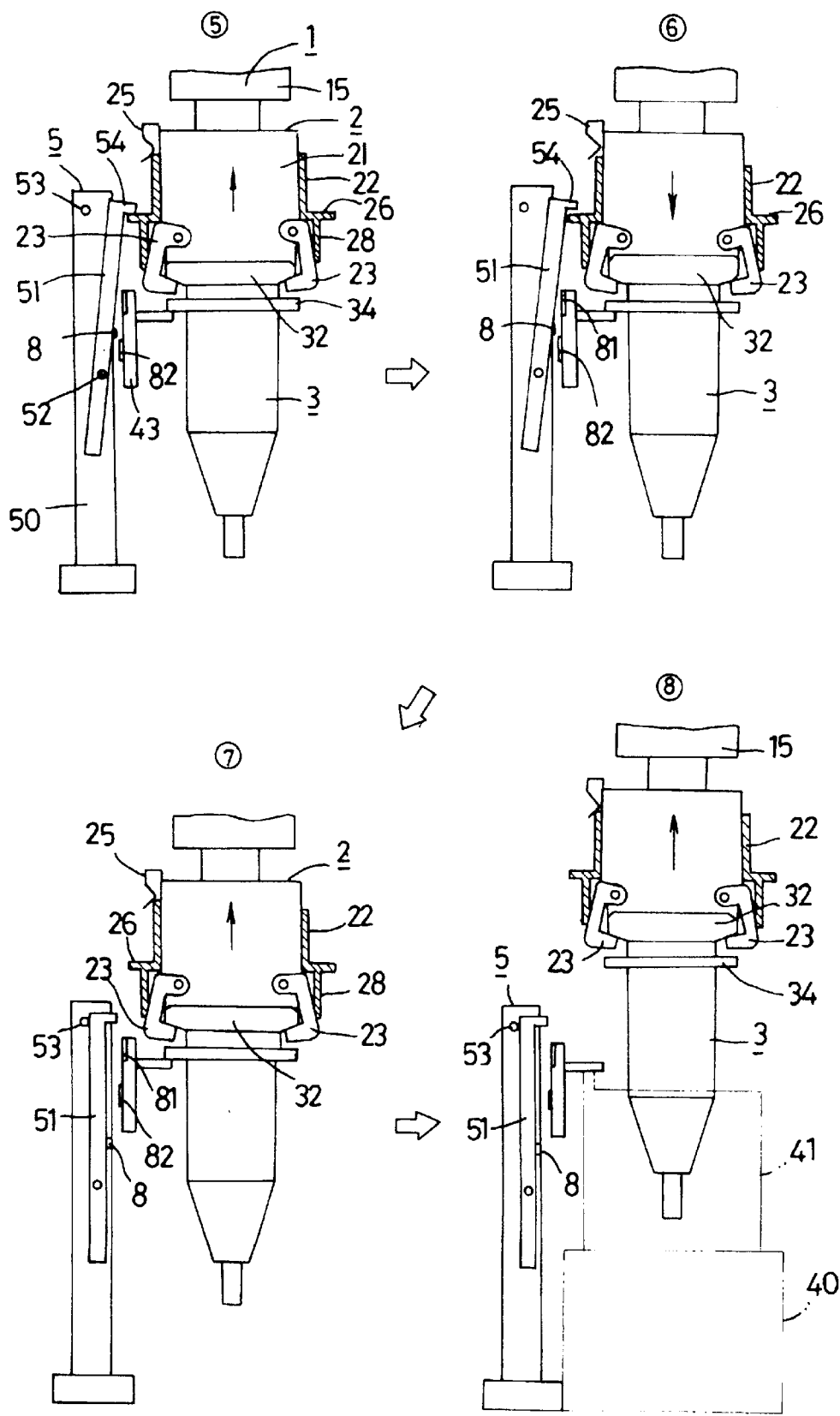
FIG. 5 a diagram showing the second half of the head holding operation.

With reference to FIG. 5, step (5), operation of the drive device 1 subsequently raises the chuck mechanism 2. With this movement, the flange 26 of the slide sleeve 22 comes into contact with the control piece 54 of the pivotal lever 51, which thereafter prevents the ascent of the sleeve 22, permitting the sleeve 22 to be lowered relative to the shaft 21. This causes the sleeve 22 to press the chuck jaws 23, 23 downward, closing the jaws 23, 23 against the tension springs 24. Consequently, the jaws 23, 23 clamp the holdable portion 32 of the pipette head 3, whereby the head 3 is held by the chuck mechanism 2.

The chuck mechanism 2 is thereafter slightly lowered as shown in FIG. 5, step (6), moving the sleeve flange 26 away from the control piece 54 of the pivotal lever 51. This movement opposes an intermediate portion between the first drive magnet 81 and the second drive magnet 82 to the driven magnet 8, and the lever 51 is turned counterclockwise by the resulting repulsive force of the two magnets.

Subsequently, the chuck mechanism 2 is raised as shown in FIG. 5, step (7). During the ascent of the chuck mechanism 2, the second drive magnet 82 is opposed to the driven magnet 8, temporarily turning the pivotal lever 51 clockwise. The control piece 54, which has moved past the flange 26 of the slide sleeve 22 by this time, is brought into contact with or opposed to the lower half portion 28. When the chuck mechanism 2 is thereafter raised further, the second drive magnet 82 and the driven magnet 8 are so positioned as to produce a repulsive force therebetween, whereby the pivotal lever 51 is returned to the counterclockwise moved position as illustrated.

The chuck mechanism 2 is further raised, whereby the pipette head 3 held by the mechanism 2 is withdrawn from the head support member 41 as shown in FIG. 5, step (8).

Pipette Head Releasing Operation

Figure 6:
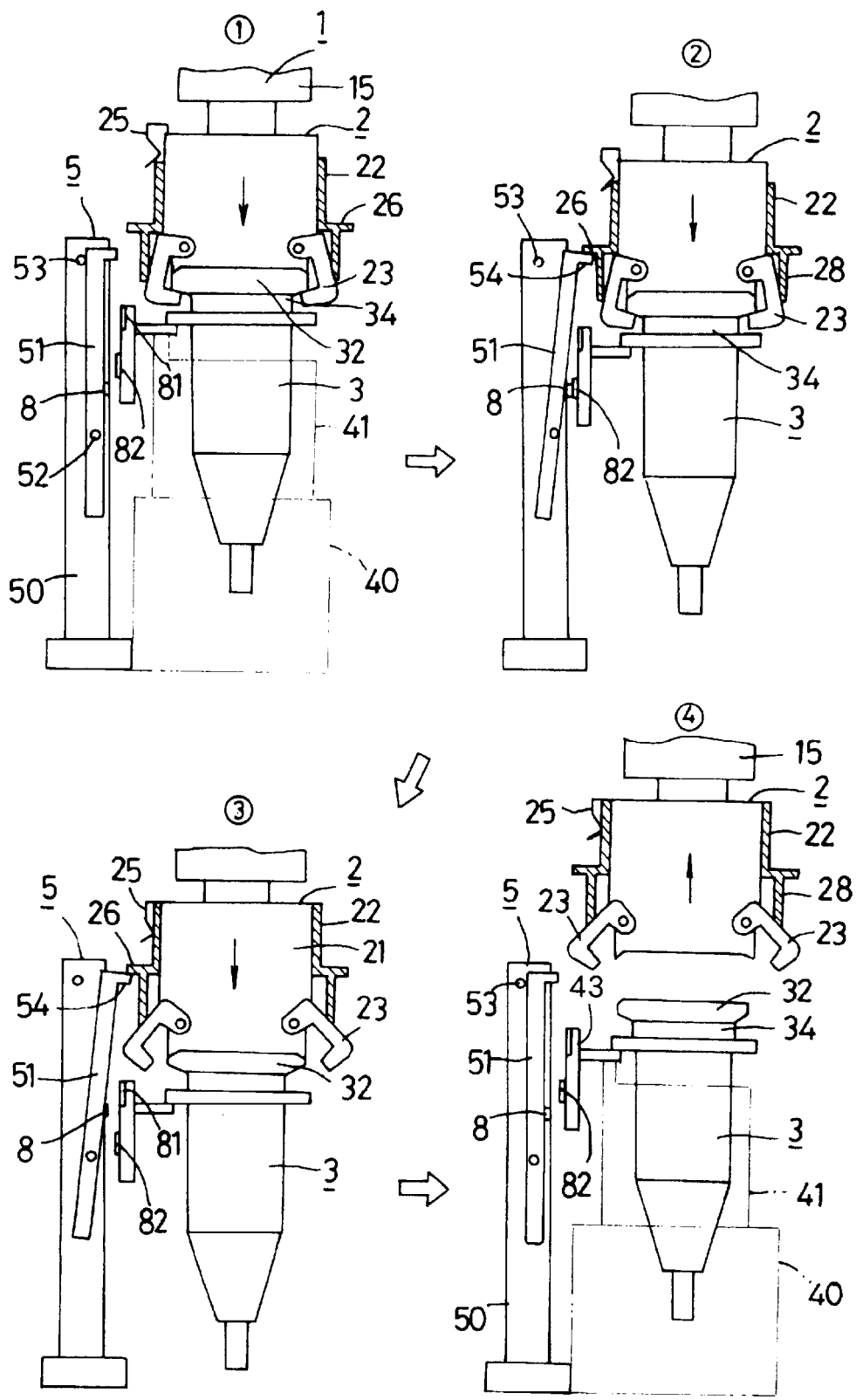
FIG. 6 is a diagram showing a head releasing operation.

With reference to FIG. 6, step (1), the chuck mechanism 2 having a pipette head 3 held thereto is lowered toward the empty head support member 41 by operating the drive device 1 to insert the head 3 into the support member 41.

As shown in FIG. 6, step (2), the pipette head 3 is further lowered, causing the second drive magnet 82 to face the driven magnet 8 and producing an attracting force between the two magnets. The force moves the lever 51 clockwise, bringing the control piece 54 into contact with the lower half portion 28 of the slide sleeve 22.

When the chuck mechanism 2 is further lowered from this state, the control piece 54 comes into contact with the flange 26 of the sleeve 22 as seen in FIG. 6, step (3), restraining the sleeve 22 from lowering. This raises the sleeve 22 relative to the shaft 21 to free the chuck jaws 23, 23. Consequently, the jaws 23, 23 open by being biased by the tension springs 24 to release the holdable portion 32 of the pipette head 3.

With reference to FIG. 6, step (4), the chuck mechanism 2 is then raised and thereby removed from the pipette head 3, which in turns remains in the head support member 41. The second drive magnet 82 and the driven magnet 8 are so positioned relative to each other that a repulsive force is produced therebetween, turning the pivotal lever 51 counterclockwise into contact with the stopper 53 and returning the lever to the initial position as illustrated.

Pipette Head replacing Operation

When one of the pipette head 3 is to be replaced by the other, the chuck mechanism 2 holding the head 3 is moved to a position above the head support member 41 which is empty, and the releasing operation shown in FIG. 6, steps (1) to (4) is performed.

The chuck mechanism 2 is thereafter moved to a position above the head support member 41 accommodating the desired pipette head 3, and the holding operation shown in FIG. 4, steps (1) to (4) and FIG. 5, steps (5) to (8) is performed.

Pipetting Operation

After one of the pipette heads 3 has been held by the chuck mechanism 2, the reciprocating drive device 1 is driven to move the pipette head 3 to above the tip holder 61 shown in FIG. 1 and thereafter lower the head 3 toward one of the pipette tips 6, whereby the tip 6 is fitted to the head 3.

The pipette head 3 carrying the tip 6 is then moved to above an unillustrated reagent container, a reagent is drawn into the pipette tip 6, the head 3 is thereafter moved to above the desired reaction container 7, and the reagent is drawn off from the tip 6 into a specified cavity 71 of the container 7.

With the pipetting apparatus embodying the invention, the pipette head 3 is automatically held by the chuck mechanism 2 and released therefrom with the movement of the mechanism 2 toward and away from the head stowing device 4. This eliminates the manual pipette head replacement procedure conventionally needed, realizing rapid replacement of the head.

With the pipette head 3 held by the chuck mechanism, the shaft 21 of the chuck mechanism 2 and the connector 34 of the head 3 are in engagement with each other in intimate contact, so that the head 3 is accurately aligned with the chuck mechanism 2 to ensure a highly accurate pipetting operation.

Liquid Level Measuring System

Figure 13:
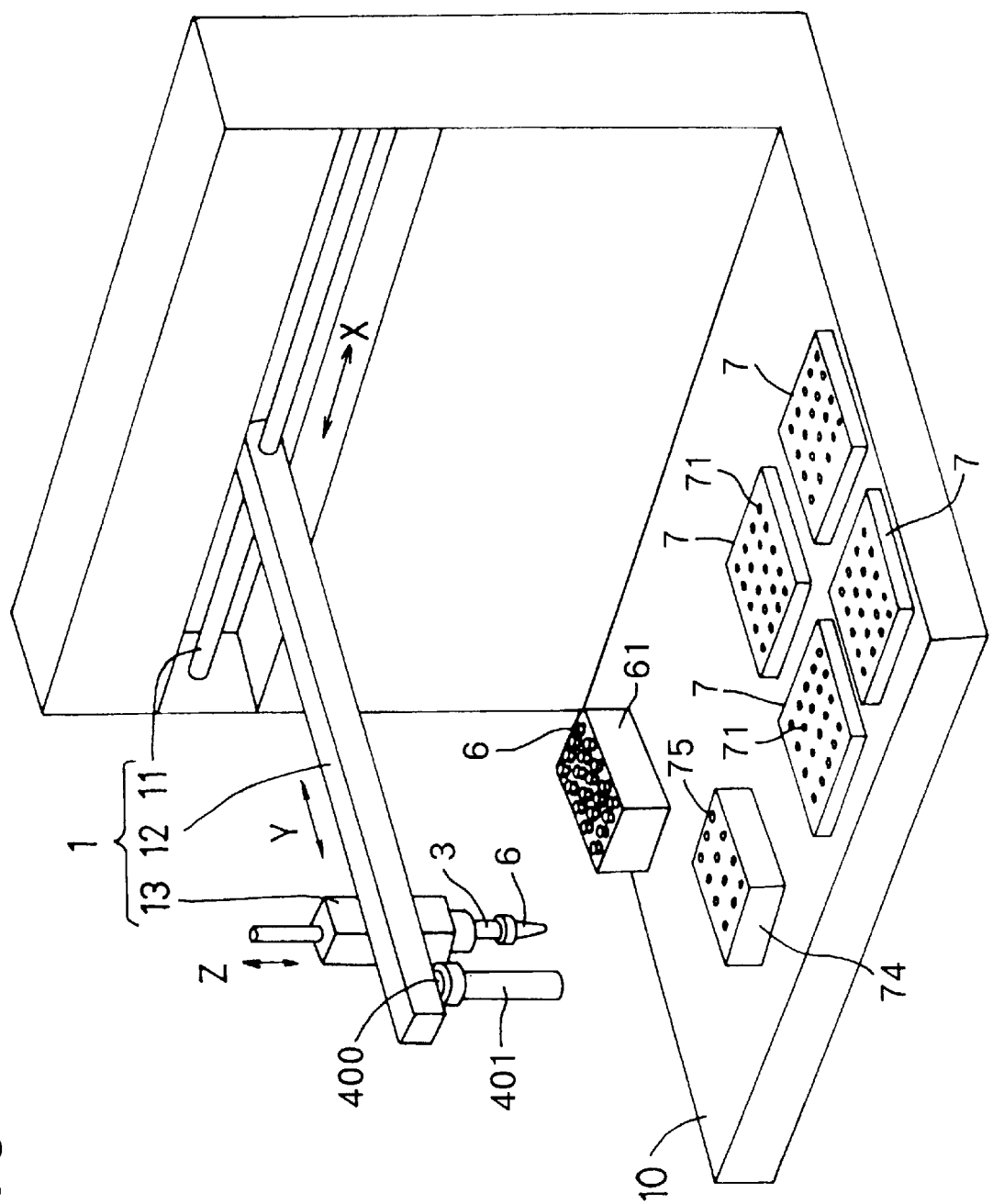
FIG. 13 is a perspective view showing the construction of a pipetting apparatus having an ultrasonic sensor.

FIG. 13 shows another pipetting apparatus of the invention which comprises a ultrasonic sensor 400 provided at one side of a pipette head 3. The pipette head 3 and the sensor 400 are movable together in the directions of three axes by being driven by a reciprocating drive device 1.

Figure 14:
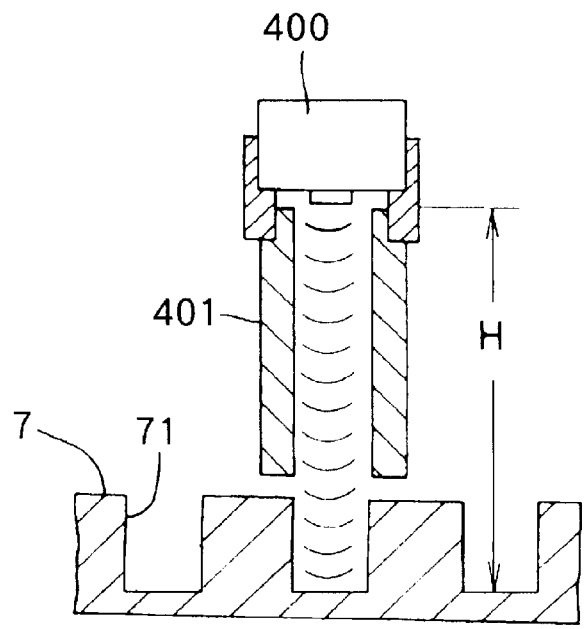
FIG. 14 is a diagram in section showing the sensor in use for distance measurement.

With reference to FIG. 14, the ultrasonic sensor 400 has a tube 401 of circular cross section vertically attached to the wave emitting portion thereof. The tube 401 has an inside diameter which is equal to the inside diameter D of the smallest of the cavities formed in the containers to be stated later, for example, 7 mm. The tube 401 is, for example, 60 mm in length.

Figure 15:
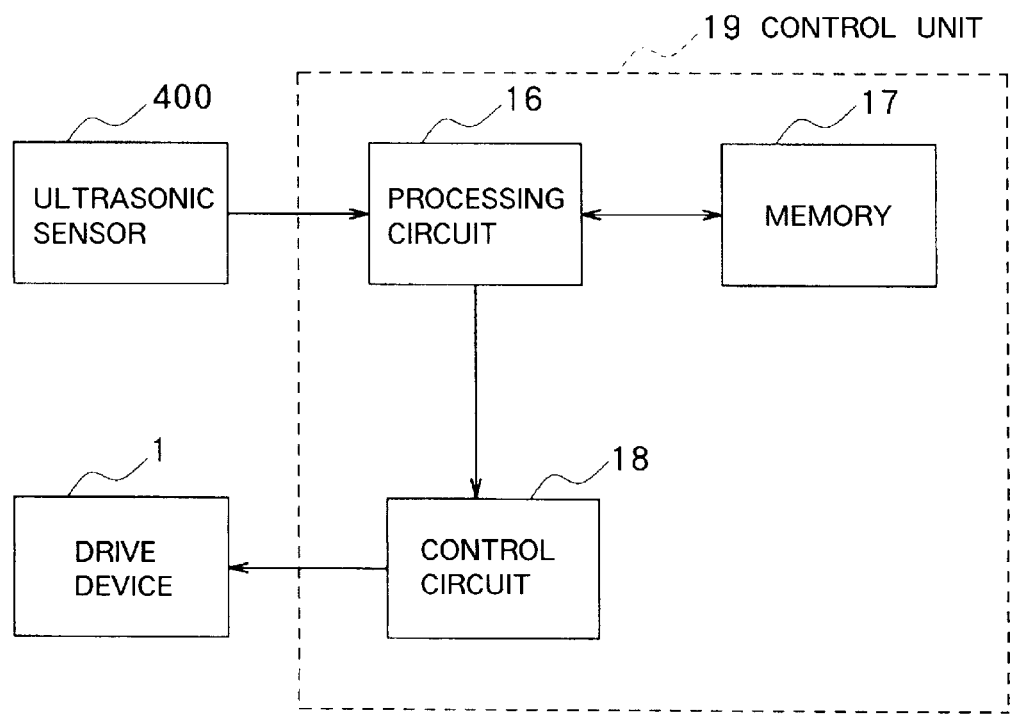
FIG. 15 is a block diagram showing the construction of a control system.

FIG. 15 shows a control unit 19 connected to the drive device 1 and the ultrasonic sensor 400. The control unit 19 comprises a processing circuit 16 for processing as specified the measurement data obtained from the sensor 400, a memory 17 for storing various items of data necessary for the processing and the result of processing, and a control circuit 18 for controlling the drive device 1.

As shown in FIG. 13, a pipette table 10 has mounted thereon a tip holder 61, reagent container 74 and reaction containers 7 each in a predetermined position. The reagent container 74 is formed in its upper surface with a plurality of cavities 75 for accommodating the reagents to be drawn into pipette tips 6. Each reaction container 7 is formed in its upper surface with cavities 71 into which the reagent within the pipette tip 6 is to be placed. The data already stored in the memory 17 includes a limit distance Hlimit which is the distance from a predetermined level to the bottom face of the cavity 71 of the reaction container 7.

In the pipetting operation, the drive device 1 is controlled to move the pipette head 3 and the ultrasonic sensor 400 and fit one of the pipette tips 6 in the tip holder 6 on the table 10 to the head first. The reagent in the cavity 75 of the reagent container 74 is then drawn into the pipette tip 6.

Next, the head 3 and the sensor 400 are moved to a position above the desired reaction container 7 to draw off the reagent from the tip 6 into the cavity 71 of the container 7. At this time, the sensor 400 first measures the distance (liquid surface distance) to the liquid surface of a reagent 72 already placed in the cavity 71 of the reaction container 7. In this case, the opening portion of the tube 401 is brought close to the opening portion of cavity 71 of the reaction container 7 to the greatest possible extent to oppose the opening portions to each other in alignment as seen in FIG. 14.

When the sensor 400 produces ultrasonic waves in this state, the waves are guided by the inner peripheral surface of the tube 401 into the cavity 71 of the reaction container 7 without diffusion. Upon reflection at the liquid surface of the reagent 72, the waves are guided again by the inner peripheral surface of the tube 401 to return to the sensor 400. The measurement data obtained by the sensor 400 is used for controlling the level of the pipette head 3 by the control unit 19 shown in FIG. 15.

Figure 16:
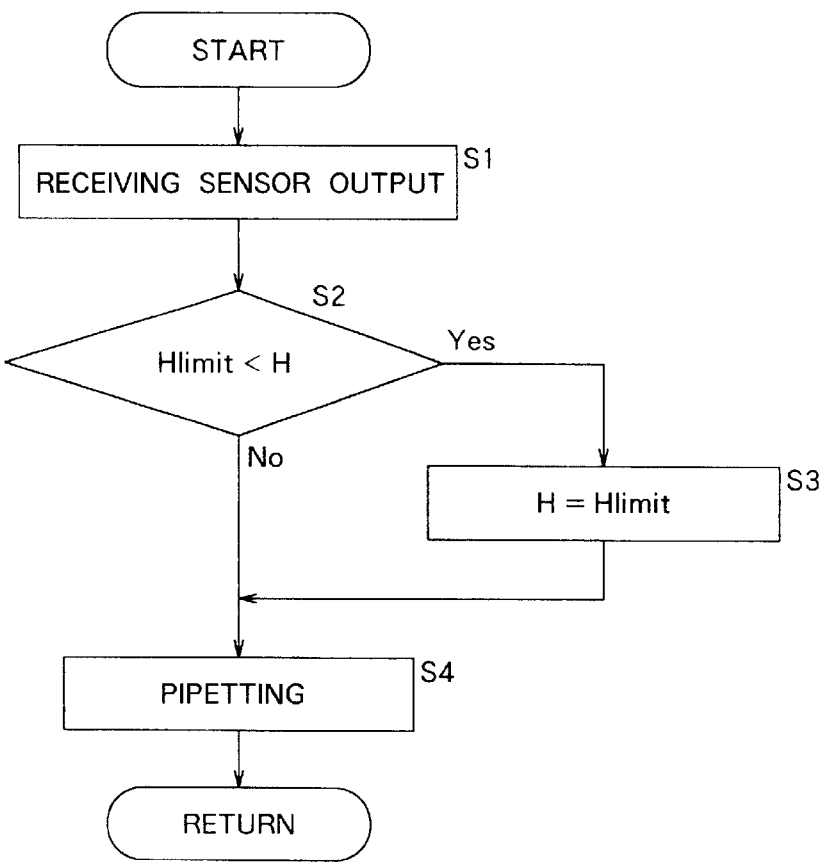
FIG. 16 is a flow chart showing the procedure to be executed for a pipetting operation.

FIG. 16 shows the procedure for operating the drive device 1 based on the measurement given by the ultrasonic sensor 400. First in step S1, the sensor output is fed to the processing circuit 16, in which the liquid surface distance H derived from the sensor output is compared with the limit distance Hlimit to inquire whether the distance H is greater than the limit distance Hlimit in step S2. When the answer is affirmative, the distance H is replaced by the limit distance Hlimit in step S3, followed by step S4 for pipetting. On the other hand, if the inquiry of step S2 is answered in the negative, step S4 immediately follows to perform a pipetting operation based on the measured distance H.

Figure 17:
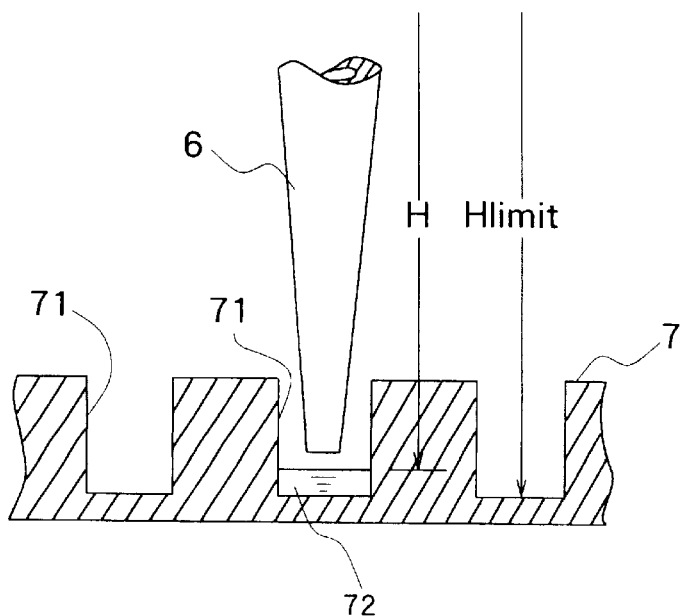
FIG. 17 is a diagram showing the step of drawing off a reagent from a pipette tip.

In the pipetting operation, the extremity of the pipette tip 6 fitted to the head 3 is positioned above the liquid level of the reagent 72, for example, 0.2 to 0.6 mm thereabove as shown in FIG. 17. The liquid surface distance H contains an error; even if the distance H is greater than the limit distance Hlimit, the pipetting operation is conducted based on the limit distance Hlimit as the liquid surface distance through the procedure of FIG. 16. It is therefore possible to avoid the situation wherein the extremity of the pipette tip descends further below the bottom face of cavity of the reaction container although it is not unlikely that the extremity will dip into the reagent in the container cavity, whereby the collision of the pipette tip is avoided.

A plunger mechanism (not show) thereafter operates to discharge the reagent in the pipette tip 6 into the cavity 71 of the reaction container 71. At this time, the reagent discharged from the tip 6 is in the form of a drop and comes into contact with the liquid surface of the reagent 72 within the container cavity 71, freeing the surface tension involved, whereby the reagent is placed dropwise into the cavity 71.

The apparatus described is adapted for pipetting without the likelihood of the pipette tip colliding with the reaction container even if an error is involved in measuring the liquid surface distance. Accidents such as damage to the pipette head are also avoidable.

Incidentally, the distance to the upper surface of the reaction container 7 can be stored in the memory 17 as a second limit distance. If the liquid surface distance measured for the pipetting operation is smaller than the second limit distance, the pipetting operation can then be performed based on the second limit distance which serves as the liquid surface distance. This realizes a normal pipetting operation with a higher probability even if an error is involved in measuring the distance.

Other Construction of Chuck Control Mechanism

Figure 18:
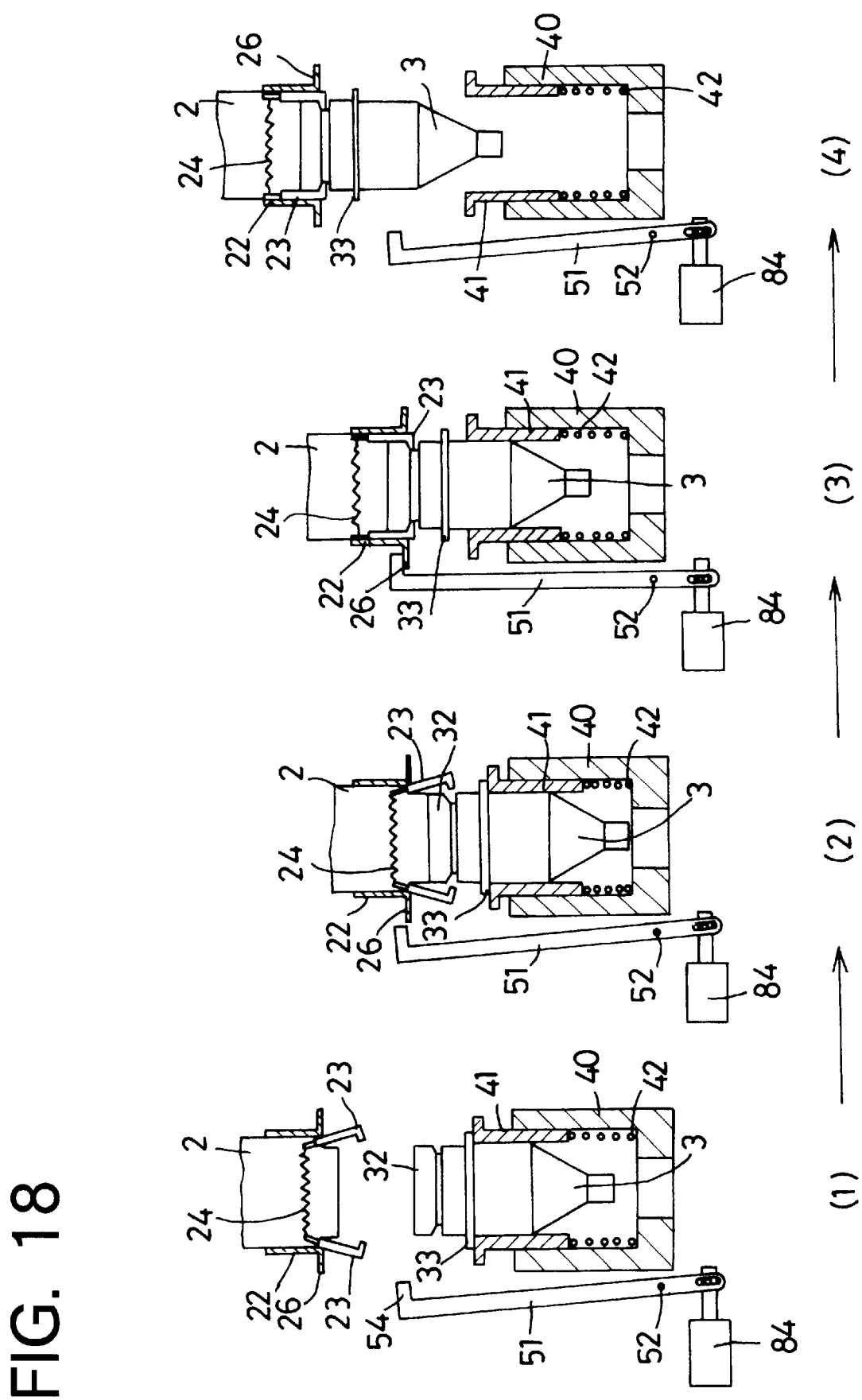
FIG. 18 is a diagram showing a head holding operation in a pipetting apparatus including a chuck control mechanism of different construction.
Figure 19:
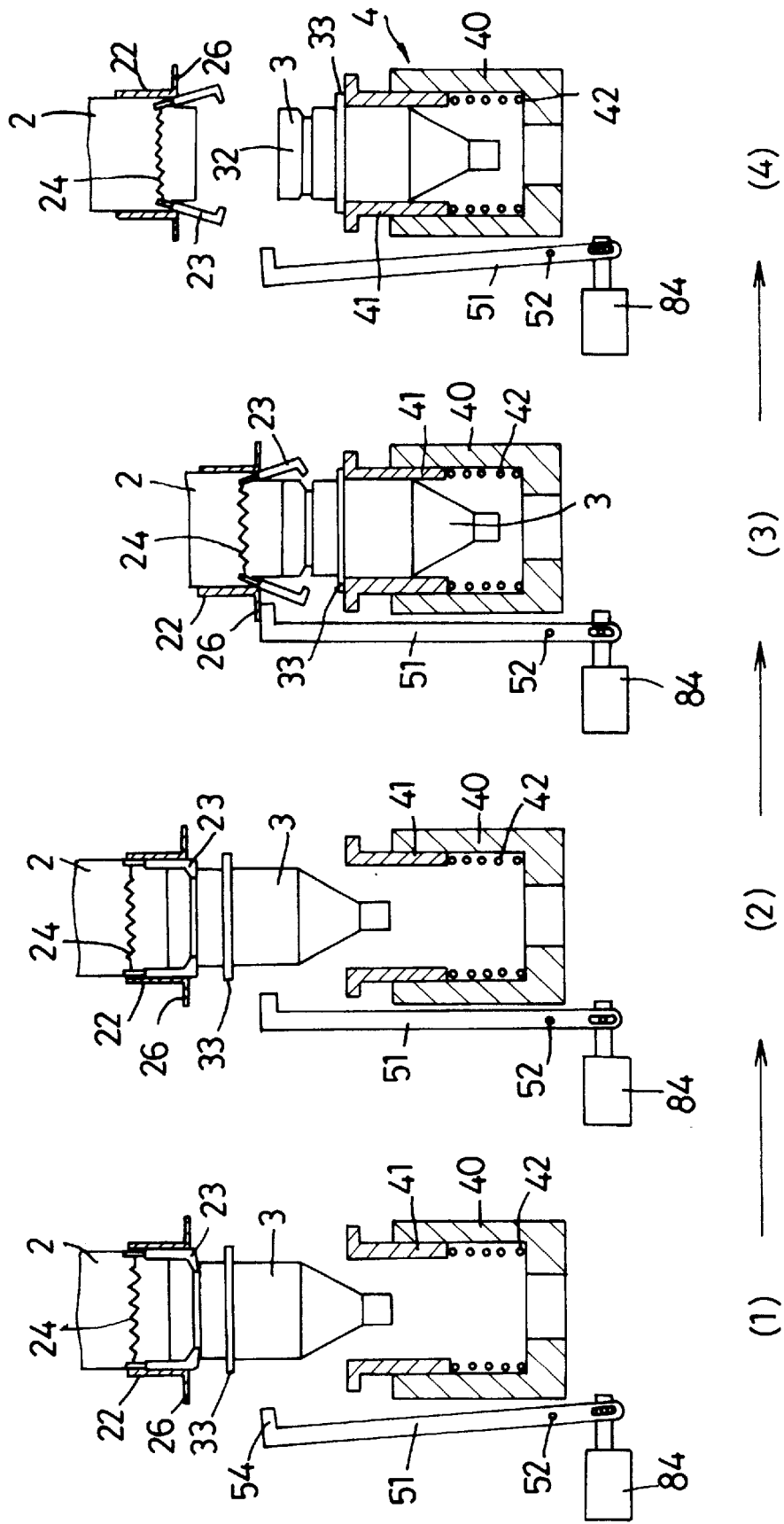
FIG. 19 is a diagram showing a head releasing operation in the pipetting apparatus.

While the magnets 8, 81, 82 provide the power source for operating the chuck mechanism 2 in the case of the foregoing chuck control mechanism 5, the power source is not limited to the magnetic means, but it is also possible to use, for example, a solenoid device 84 as the power source as seen in FIGS. 18 and 19. In FIG. 2 and these drawings, basically like parts are designated by like reference numerals.

With reference to FIGS. 18 and 19, the pivotal lever 51 has a base end which is connected to the output end of the solenoid device 84. When operated, the device 84 drives the pivotal lever 51 to effect a holding operation (FIG. 18) and a releasing operation (FIG. 19) in the same manner as the holding and releasing operations shown in FIGS. 4 to 6.

More specifically stated with reference to FIG. 18, the chuck mechanism 2 descends with the chuck jaws 23, 23 opened as shown in step (1) and comes into contact with the pipette head 3 as shown in step (2). In this state, the solenoid device 84 operates, turning the pivotal lever 51 clockwise and bringing the control piece 54 into engagement with the upper surface of the flange 26 as seen in step (3). The chuck mechanism 2 slightly ascends in this state, whereby the slide sleeve 22 is relatively lowered to close the chuck jaws 23, 23. As shown in step (4), the pivotal lever 51 is moved counterclockwise by the operation of the solenoid device 84, permitting the chuck mechanism 2 and the head 3 to move upward.

In the releasing operation shown in FIG. 19, the chuck mechanism 2 descends, with the pipette head 3 held by the chuck jaws 2, 23 as closed as seen in step (1). In step (2), the solenoid device 84 operates, moving the pivotal lever 51 clockwise approximately to a vertical position. Further in step (3), descent of the chuck mechanism 2 moves the control piece 54 of the lever 51 into engagement with the lower surface of flange 26 of the slide sleeve 22. The chuck mechanism 2 further descends from this state, permitting the slide sleeve 22 to rise relatively to open the chuck jaws 23, 23. The pivotal lever 51 is thereafter moved counterclockwise by the operation of the solenoid device 84, the chuck mechanism 2 moves up, and the head 3 is accommodated in the head stowing device 4 as seen in step (4).

Other Constructions of Chuck Mechanism and Chuck Control Mechanism

Figure 20:
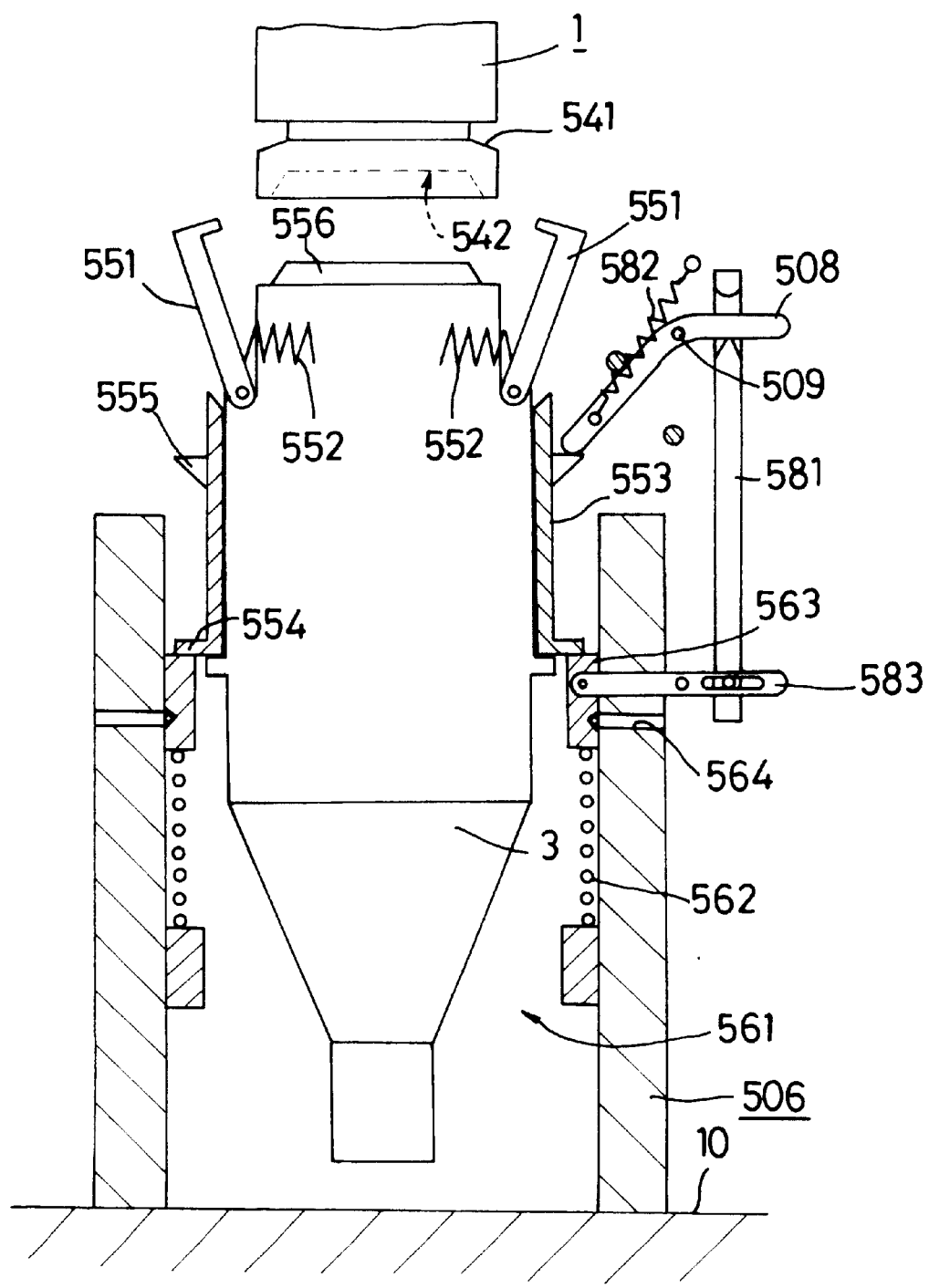
FIG. 20 is an enlarged fragmentary front view partly broken away and showing a pipetting apparatus having a chuck mechanism and a chuck control mechanism of different construction.

FIG. 20 shows a pipetting apparatus wherein a chuck mechanism comprising a slide sleeve 553, chuck jaws 551, 551, etc. is attached to a pipette head 3.

When not in use, the pipette head 3 is accommodated in a head stowing device 506, which is centrally formed with a space 561 for receiving the head 3 and has an inner hollow cylinder 563 biased upward by a spring 562. The cylinder 563 is provided with a ball plunger 564 for restraining the movement of the slide sleeve 553 when the pipette head 3 is lowered. A reciprocating drive device 1 has an output end formed with a groove 541. On the other hand, the chuck jaws 551, 551 which are fittable in the groove 541 are attached to upper end portions of the head 3 and biased to open by springs 552, 552. The sleeve 553 is formed at its lower end with a flange 554 which is adapted to bear on the upper end face of the cylinder 563.

The output end of the drive device 1 has a recess 542 in its lower end face, while a protrusion 556 is formed on the top of the head 3. The protrusion 556 is fittable in the recess 542, thereby correcting the displacement of the head 3 and joining the head to the output end with improved stability.

A release lever 508 is movably supported by a pivot 509 and biased into clockwise rotation by a lever return spring 582 to provide a chuck control mechanism. The lever 508 has one free end extending toward a projection 555 on the slide sleeve 553 and the other free end in engagement with an upper end portion of a vertical bar 581. The vertical bar 581 has a lower end portion in engagement with a slotted portion of one end of a horizontal bar 583. The other end of the horizontal bar 583 is connected to the inner cylinder 563.

When the cylinder 563 moves upward or downward, therefore, this movement is transmitted to the release lever 508 through the horizontal bar 583 and the vertical bar 581, turning the release lever 508.

Figure 21:
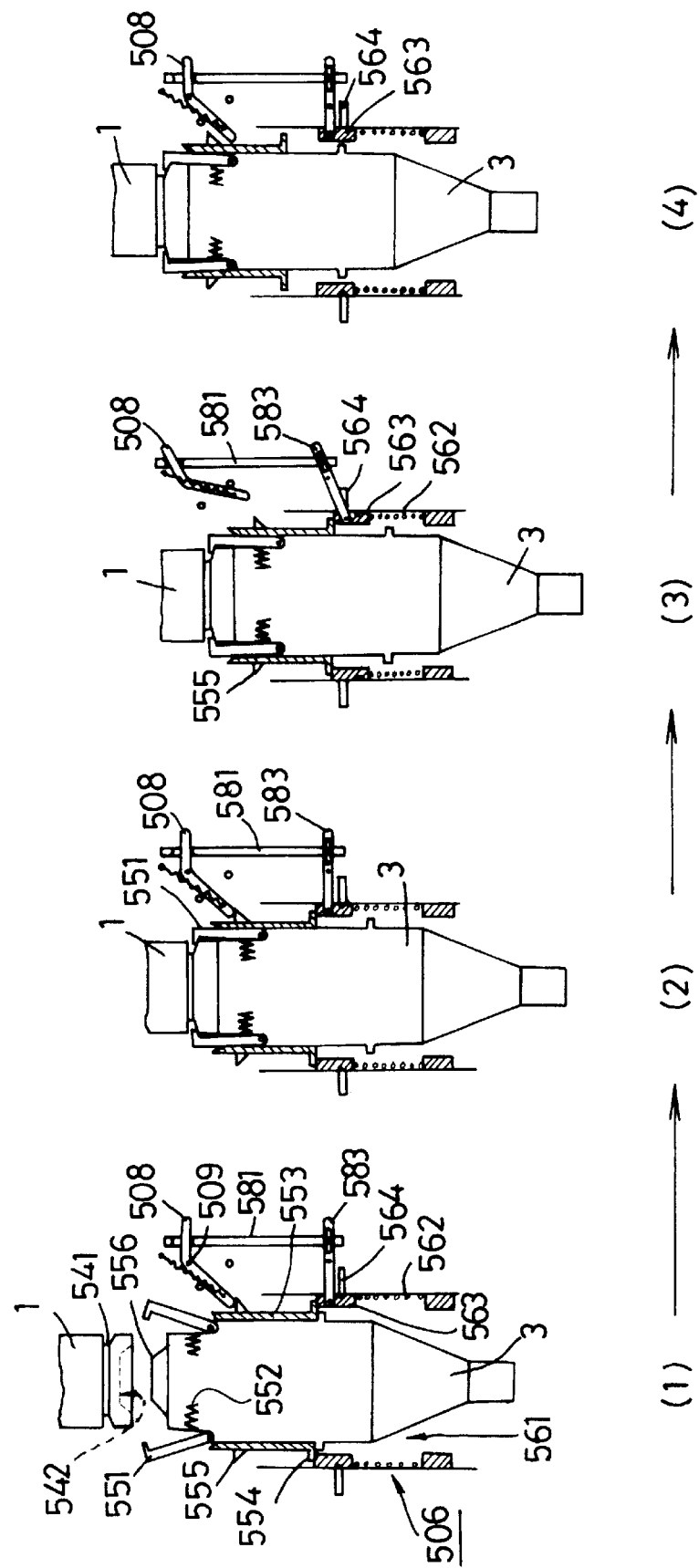
FIG. 21 is a diagram showing a head holding operation in the pipetting apparatus.

With the apparatus described, the pipette head 3 is held to the drive device output end by the steps shown in FIG. 21. In the initial state shown in step (1), the chuck jaws 551, 551 are open, the inner free end of the release lever 508 is in contact with the projection 555 on the slide sleeve 553, and the lower end of the sleeve 555 is in contact with the upper end face of the inner cylinder 563. The output end of the drive device 1 is lowered in this state into contact with the pipette head 3 and further lowered, permitting the slide sleeve 553 to move upward relative to the output end to close the jaws 551, 551, whereby the head 3 is held to the output end as shown in step (2).

When the output end of the drive device 1 in this state is further lowered, the inner cylinder 563 is disengaged from the ball plunger 564 to lower against the action of the spring 562 as shown in step (3). This movement turns the horizontal bar 583, moving the vertical bar 581 upward at the same time and turning the release lever 508 counterclockwise. The lever 508 is moved away from the projection 555 of the sleeve 555.

The pipette head 3 is thereafter raised by the operation of the drive device 1 as seen in step (4). With this movement, the cylinder 563 also rises, permitting the release lever 508 to return to the original position.

Figure 22:
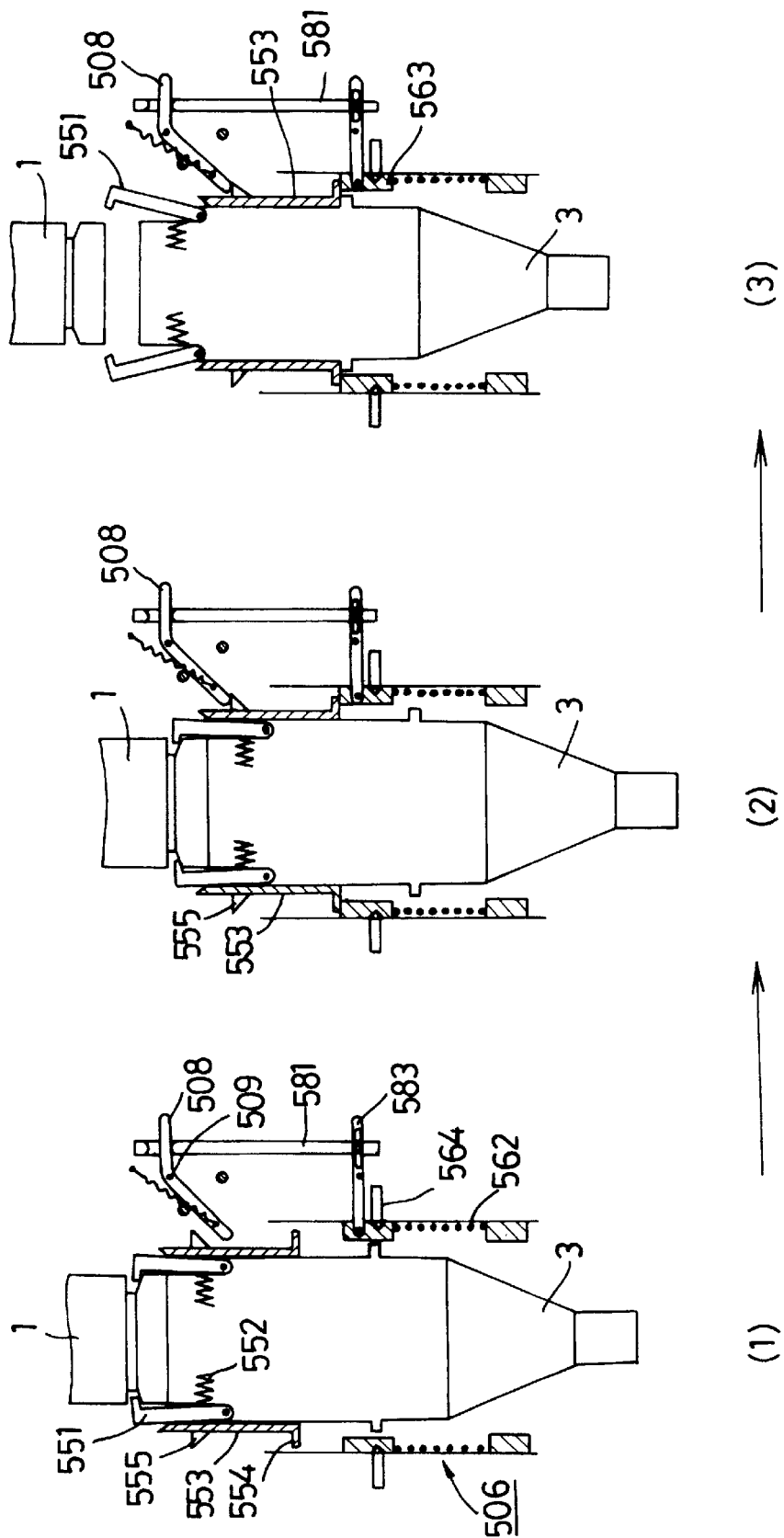
FIG. 22 is a diagram showing a head releasing operation in the pipetting apparatus.

To release the pipette head 3 from the output end, the head 3 is lowered toward the head stowing device 506 by the operation of the drive device 1 as seen in FIG. 22, step (1). This causes the projection 555 of the slide sleeve 553 to move past the inner free end of the release lever 508 by turning the lever as shown in step (2).

When the pivotal head 3 is raised by the operation of the drive device 1 in this state, the inner end of the release lever 508 comes into contact with the upper end face of the projection 555, preventing the ascent of the sleeve 553. Consequently, the slide sleeve 553 descends relative to the output end of the drive device 1, opening the chuck jaws 551, 551 and releasing the pipette head 3 from the output end.

Hand Mechanism

Figure 23:
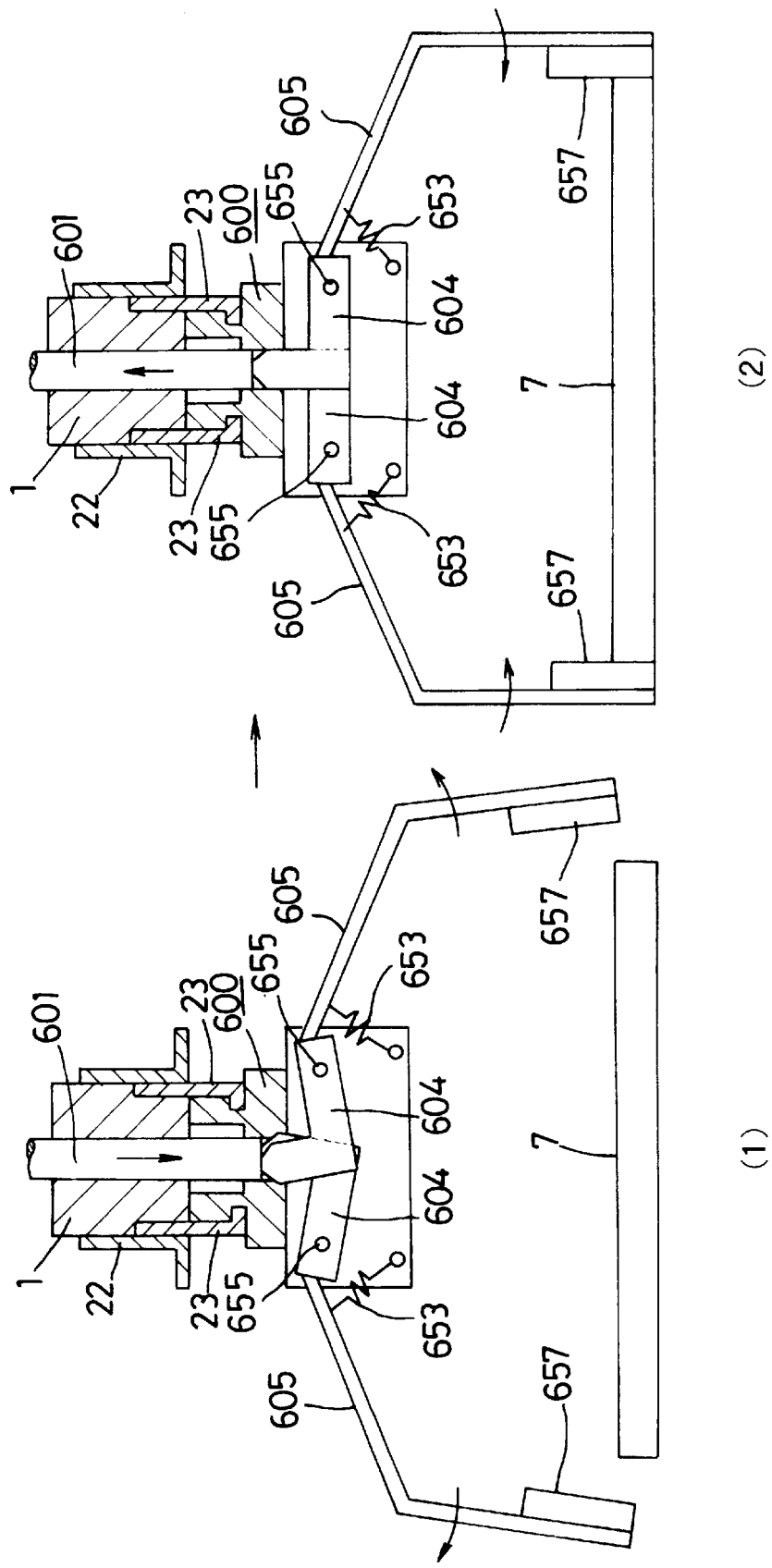
FIG. 23 is a diagram showing the construction of main portion of a pipetting apparatus having a hand mechanism and the operation of the apparatus.
Figure 24:
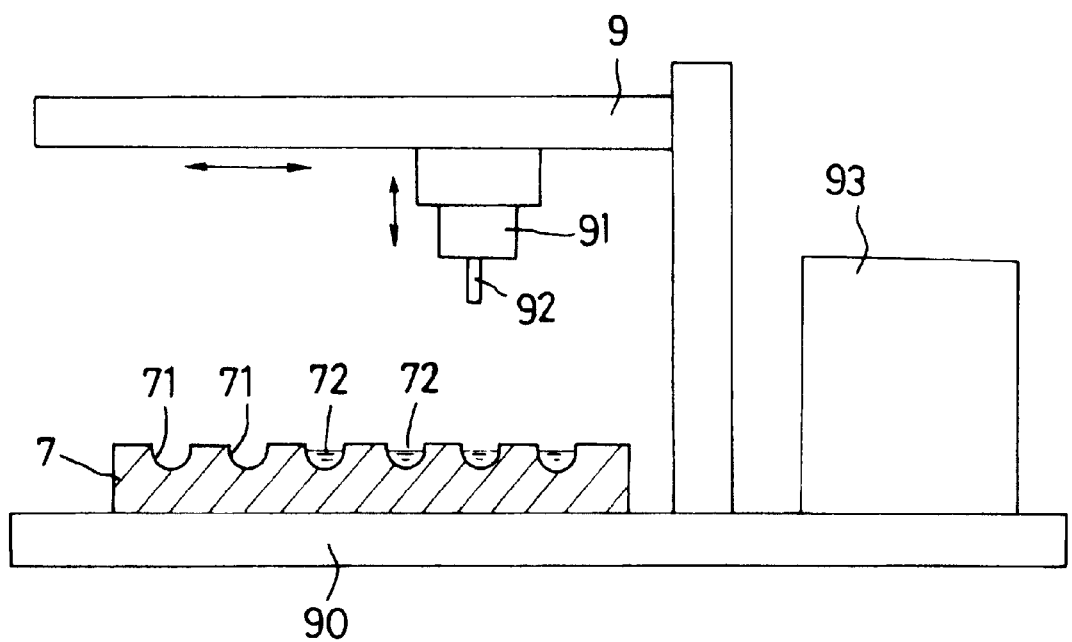
FIG. 24 is a front view partly broken away and generally showing the construction of a conventional pipetting apparatus.

With the conventional pipetting apparatus, the reaction container on the pipette table is manually replaced by another after the completion of the pipetting operation, so that the apparatus has the problem of necessitating a cumbersome procedure. The present embodiment therefore provides simple means for automatically replacing the reaction container. With reference to FIG. 23, a hand mechanism 600 for clamping the reaction container 7 is removably attached to the output end of the drive device 1 in place of the pipette head described. According to the present embodiment, the output end of the drive device 1 is provided with a piston 601 constituting a plunger mechanism and reciprocally drivable for the drawing-in and discharging operations of the pipette head.

The hand mechanism 600 has a head portion which, like the pipette head described, can be held by and released from chuck jaws 23, 23. A pair of L-shaped pivotal members 604, 604 are movably attached by respective pivots 655, 655 to lower end portions of the hand mechanism 600. Each pivotal member 604 has an inner free end extending to the lower end of the piston 601 and an outer free end provided with a finger member 605. The reaction container 7 can be clamped by the pair of finger members 605; 605 at its opposite sides. Each finger member 605 has a cushion member 657 attached to its outer end for reducing impact when clamping the container 7. The finger members 605, 605 are biased toward a closed position by respective springs 653, 653.

Accordingly, the pair of finger members 605, 605 are opened against the springs 653, 653 by lowering the piston 601 as shown in FIG. 23, step (1). When the piston 601 is thereafter raised, the finger members 605, 605 are closed by the action of the springs 653, 653 to clamp the container 7 as seen in step (2).

According to the above embodiment, one of the hand mechanism and the pipette head is usable by replacement to automatically carry out a sequence of operations starting with a change of reaction container and ending with a pipetting operation.

What is claimed is:

1. A pipetting apparatus comprising:
   a container mount for installing thereon one or a plurality of containers for a reagent to be withdrawn from or placed in,
   a head stowing device having accommodated therein one or a plurality of pipette heads for drawing in and discharging the reagent,
   a drive device for reciprocatingly moving an output end between the container mount and the head stowing device,
   a chuck mechanism attached to the output end of the drive device or to the pipette head for holding the pipette head to the output and of the drive device and releasing pipette head from the output end, and
   a chuck control mechanism disposed in the vicinity of a head stowage or each of head stowages of the head stowing device for causing the chuck mechanism to perform the holding operation and the releasing operation with the movement of the output end of the drive device toward or away from one head stowage of the head stowing device,
   the chuck mechanism being attached to the output end of the drive device, and including a control piece engageable with and disengageable from the chuck mechanism to effect the holding operation and the releasing operation, and magnet means for moving the control piece with the movement of the chuck mechanism when the chuck mechanism moves the pipette head held thereby toward or away from one head stowage of the head stowing device.

2. A pipetting apparatus as defined in claim 1 wherein the chuck mechanism comprises a shaft attached to the output end of the drive device, a plurality of chuck jaws pivoted to an end portion of the shaft for clamping the pipette head, a slide sleeve fitting around the shaft and slidable thereon for opening and closing the chuck jaws, and holding means movable with the sliding movement of the slide sleeve for holding the slide sleeve at a first slid position wherein the chuck jaws are open and a second slid position wherein the chuck jaws are closed.

3. A pipetting apparatus as defined in claim 1 wherein the chuck mechanism comprises a plurality of jaws for holding a base end of the pipette head from therearound, and rotation preventing means is provided at a junction of the chuck mechanism and the pipette head for preventing the rotation of the pipette head as held by the chuck mechanism.

4. A pipetting apparatus as defined in claim 3 wherein the rotation preventing means is provided with means for adjusting the angle of rotation, relative to the chuck mechanism, of the pipette head as held by the chuck mechanism.

5. A pipetting apparatus as defined in claim 1 wherein the chuck mechanism comprises a plurality of chuck jaws for holding the pipette head and opening-closing means for opening and closing the chuck jaws with the reciprocating movement of the chuck mechanism by the operation of the drive device, the chuck mechanism having coupled thereto first sensor means for detecting the pipette head as joined to the chuck mechanism and second sensor means for detecting the chuck jaws as closed by the opening-closing means.

6. A pipetting apparatus as defined in claim 5 wherein the first sensor means and the second sensor means have connected thereto means for notifying the operator of the result of detection obtained by each sensor means.

7. A pipetting apparatus as defined in claim 1 wherein a distance sensor is provided as directed downward at one side of the pipette head for measuring the distance to an object, the distance sensor having connected thereto a control unit for controlling the operation of the drive device, the control unit comprising a data memory having stored therein a limit distance in accordance with the distance to bottom faces of a plurality of cavities formed in a reaction container for the liquid to be placed in, a first controller for executing a procedure for measuring the distance to the liquid surface in the specified cavity of the reaction container for the liquid to be placed in, and a second controller for comparing the liquid surface distance obtained by the operation of the first controller with the limit distance stored in the data memory and executing a pipetting operation based on the limit distance when the liquid surface distance is greater than the limit distance.

8. A pipetting apparatus as defined in claim 7 wherein the data memory has further stored therein a second limit distance in accordance with the distance to an upper surface of the reaction container for the liquid to be placed in, and the second controller compares the liquid surface distance obtained by the operation of the first controller with the second limit distance stored in the data memory and executes the pipetting operation based on the second limit distance as the liquid surface distance when the liquid surface distance is smaller than the second limit distance.

9. A pipetting apparatus as defined in claim 1 wherein the chuck mechanism is attached to the pipette head, and the chuck control mechanism causes the chuck mechanism to perform the holding operation and the releasing operation with the upward and downward movement of the pipette head.

10. A pipetting apparatus as defined in claim 9 wherein the chuck mechanism comprises a plurality of chuck jaws for clamping the output end of the drive device and opening-closing means for opening and closing the chuck jaws, and the chuck control mechanism is engageable with and disengageable from the opening-closing means to open and close the chuck jaws.

11. A pipetting apparatus as defined in claim 1 wherein the chuck mechanism is attached to the output end of the drive device, and the chuck control mechanism comprises drive magnet means movable along a specified path with the movement of the chuck mechanism when the chuck mechanism moves the pipette head held thereby toward or away from one head stowage of the head stowing device, driven magnet means disposed as opposed to the drive magnet means and reciprocatingly movable along a specified path by a magnetic attracting force or magnetic repulsive force produced between the drive magnet means and the driven magnet means with the movement of the drive magnet means, and a control piece connected to the driven magnet means and engageable with and disengageable from the chuck mechanism with the reciprocating movement of the driven magnet means to effect the holding operation and the releasing operation.

12. A pipetting apparatus as defined in claim 11 wherein the chuck mechanism comprises a plurality of chuck jaws for clamping the pipette head and opening-closing means for opening and closing the chuck jaws, and the control piece of the chuck control mechanism is engageable with and disengageable from the opening-closing means to open and close the chuck jaws.

13. A pipetting apparatus as defined in claim 11 wherein each of the head stowages of the head stowing device comprises a head support member for supporting the pipette head, and a spring for elastically supporting the head support member in a vertical direction, the drive magnet means comprising a magnet holder attached to the head support member, and a first drive magnet and a second drive magnet arranged respectively on an upper portion and a lower portion of the magnet holder, the driven magnet means comprising a pivotal lever supported pivotally in a vertical plane within a specified angular range and a driven magnet attached to the pivotal lever, the control piece projecting from one end of the pivotal lever.

14. A pipetting apparatus as defined in claim 13 wherein the first drive magnet, the second drive magnet and the driven magnet are arranged to have such position relation and polarity relation that the first or second drive magnet and the driven magnet attract each other when opposed to each other at the same level with an upward or downward movement of the magnet holder, and that the first or second drive magnet and the driven magnet repel each other when obliquely opposed to each other at slightly different levels with said movement of the magnet holder.

* * * * *

UNITED STATES PATENT AND TRADEMARK OFFICE
CERTIFICATE OF CORRECTION

PATENT NO. : 5,906,795

DATED : May 25, 1999

INVENTOR(S) : Nakashima et al.

It is certified that error appears in the above-identified patent and that said Letters Patent is hereby corrected as shown below:

Delete Column 18, line 38, (and), -- insert -- " end "

Signed and Sealed this

Fourth Day of April, 2000

Attest:

Attesting Officer

Q. TODD DICKINSON

Director of Patents and Trademarks